US012797066B2

(12) United States Patent
Ritz et al.

(10) Patent No.: US 12,797,066 B2
(45) Date of Patent: Nov. 17, 2026

(54) ORTHOPEDIC COMPRESSION IMPLANTS AND DEVICES FOR INSTALLING AND RETAINING SAME

(71) Applicants: Joseph Paul Ritz, Castroville, TX (US); Eric Alberto Marcano, San Antonio, TX (US)

(72) Inventors: Joseph Paul Ritz, Castroville, TX (US); Eric Alberto Marcano, San Antonio, TX (US)

(73) Assignee: 210 DYNAMIC, LLC, San Antonio, TX (US)

(*) Notice: Subject to any disclaimer, the term of this patent is extended or adjusted under 35 U.S.C. 154(b) by 253 days.

(21) Appl. No.: 18/014,215

(22) PCT Filed: Jul. 6, 2021

(86) PCT No.: PCT/US2021/040544
§ 371 (c)(1),
(2) Date: Jan. 3, 2023

(87) PCT Pub. No.: WO2022/010920
PCT Pub. Date: Jan. 13, 2022

(65) Prior Publication Data

US 2023/0255623 A1 Aug. 17, 2023

Related U.S. Application Data

(60) Provisional application No. 63/048,269, filed on Jul. 6, 2020.

(51) Int. Cl.
*A61B 17/064* (2006.01)
*A61B 17/00* (2006.01)
(Continued)

(52) U.S. Cl.
CPC .................... *A61B 17/0642* (2013.01); *A61B 2017/00477* (2013.01); *A61B 2017/00867* (2013.01);
(Continued)

(58) Field of Classification Search
CPC ............ A61B 17/0642; A61B 17/0682; A61B 17/064; A61B 17/0644; A61B 17/068;
(Continued)

(56) References Cited

U.S. PATENT DOCUMENTS

| | | | |
|---|---|---|---|
| 6,554,852 | B1 | 4/2003 | Oberlander |
| 8,584,853 | B2 | 11/2013 | Knight et al. |

(Continued)

FOREIGN PATENT DOCUMENTS

| | | | |
|---|---|---|---|
| CN | 105213072 | A | 1/2016 |
| WO | 2021/202008 | A1 | 10/2021 |

OTHER PUBLICATIONS

PCT/US2021/040544 International Search Report and Written Opinion dated Oct. 19, 2021 (15 p.).

(Continued)

*Primary Examiner* — Marcela I. Shirsat
(74) *Attorney, Agent, or Firm* — CONLEY ROSE, P.C.

(57) ABSTRACT

A shape-memory alloy orthopedic implant includes a bridge having a curved longitudinal axis, a first end, and a second end opposite the first end. The bridge has a radially outer surface extending axially from the first end to the second end. In addition, the orthopedic implant includes a first leg extending from the first end of the bridge. The first leg has a central axis, a fixed end fixably attached to the bridge, a free end distal the bridge, and a radially outer surface extending axially from the fixed end of the first leg to the free end of the first leg. Further, the orthopedic implant includes a second leg extending from the second end of the bridge. The second leg has a central axis, a fixed end fixably (Continued)

attached to the bridge, a free end distal the bridge, and a radially outer surface extending axially from the fixed end of the second leg to the free end of the second leg. The radially outer surface of the bridge defines a first outer profile in a cross-section of the bridge taken in a plane oriented perpendicular to the longitudinal axis of the bridge. The radially outer surface of the first leg defines a second outer profile in a cross-section of the first leg taken in a plane oriented perpendicular to the central axis of the first leg. The first outer profile has a different geometry than the second outer profile.

30 Claims, 18 Drawing Sheets

(51) Int. Cl.

| | |
|---|---|
| ***A61B 17/068*** | (2006.01) |
| ***A61B 17/08*** | (2006.01) |
| ***A61F 2/30*** | (2006.01) |
| ***A61L 27/06*** | (2006.01) |
| ***A61L 27/50*** | (2006.01) |

(52) U.S. Cl.

CPC ... *A61B 2017/0641* (2013.01); *A61B 17/0644* (2013.01); *A61B 2017/0645* (2013.01); *A61B 17/0682* (2013.01); *A61B 17/0684* (2013.01); *A61B 17/0686* (2013.01); *A61B 17/083* (2013.01); *A61F 2002/30092* (2013.01); *A61F 2002/30187* (2013.01); *A61L 27/06* (2013.01); *A61L 27/50* (2013.01); *A61L 2400/16* (2013.01)

(58) Field of Classification Search

CPC . A61B 17/0684; A61B 17/0686; A61B 17/08; A61B 17/083; A61B 2017/0477; A61B 2017/00867; A61B 2017/0641; A61B 2017/0648; A61L 27/06; A61L 27/50; A61L 27/0645; A61L 27/00867; A61L 27/0641; A61L 2400/16; A61F 2002/30092; A61F 2002/30113; A61F 2002/30187

USPC ........................................................... 606/75

See application file for complete search history.

(56) References Cited

U.S. PATENT DOCUMENTS

| | | | | |
|---|---|---|---|---|
| D705,930 | S | 5/2014 | Cheney | |
| 8,951,254 | B2 | 2/2015 | Mayer et al. | |
| 9,402,624 | B1 | 8/2016 | Scott et al. | |
| 9,585,656 | B2 | 3/2017 | Taber et al. | |
| 10,016,198 | B2 | 7/2018 | Morgan et al. | |
| 10,335,219 | B2 | 7/2019 | Mayer | |
| 10,820,902 | B2 | 11/2020 | Cheney | |
| 10,842,487 | B2 | 11/2020 | Ritz et al. | |
| 10,849,618 | B2 | 12/2020 | Cheney et al. | |
| 11,006,949 | B2 | 5/2021 | Daniel | |
| 11,020,110 | B1 | 6/2021 | Blair et al. | |
| 11,116,499 | B1 | 9/2021 | Blair et al. | |
| 11,571,206 | B2 | 2/2023 | Coleman et al. | |
| 2002/0111641 | A1* | 8/2002 | Peterson | A61B 17/083 606/157 |
| 2006/0167459 | A1 | 7/2006 | Groiso | |
| 2008/0015598 | A1 | 1/2008 | Prommersberger | |
| 2008/0065153 | A1* | 3/2008 | Allard | A61B 17/0642 606/219 |
| 2011/0313437 | A1 | 12/2011 | Yeh | |
| 2012/0241504 | A1 | 9/2012 | Soltz et al. | |
| 2013/0231667 | A1* | 9/2013 | Taylor | A61B 17/8004 606/75 |
| 2016/0199060 | A1* | 7/2016 | Morgan | A61B 17/068 227/175.1 |
| 2016/0338697 | A1 | 11/2016 | Biedermann et al. | |
| 2017/0065275 | A1* | 3/2017 | Cheney | A61B 17/064 |
| 2017/0065276 | A1* | 3/2017 | Weiner | A61B 17/0642 |
| 2017/0065278 | A1* | 3/2017 | Stone | A61B 17/0401 |
| 2017/0196678 | A1 | 7/2017 | Park et al. | |
| 2017/0340777 | A1 | 11/2017 | Ma et al. | |
| 2019/0046182 | A1 | 2/2019 | Krumme | |
| 2019/0133662 | A1 | 5/2019 | Knight et al. | |
| 2020/0197005 | A1 | 6/2020 | Daniel | |

OTHER PUBLICATIONS

PCT/US2021/040544 Response to Written Opinion dated Oct. 19, 2021 and Article 19 Amendments; Response filed Dec. 20, 2021 (18 p.).
European Search Report dated May 2, 2024, for European Application No. 21836889.2 (9 p.).
Stryker Brochure: “EasyClip Osteosynthesis Compression Staples,” 2015 (20 p.).
European Office Action dated Jun. 11, 2026, for European Application No. 21836889.2 (7 p.).
Australian Examination Report dated Jun. 12, 2026, for Australian Application No. 2021306272 (4 p.).

* cited by examiner

ORTHOPEDIC COMPRESSION IMPLANTS AND DEVICES FOR INSTALLING AND RETAINING SAME

CROSS-REFERENCE TO RELATED APPLICATIONS

This application is a 35 U.S.C. § 371 national stage application of PCT/US2021/040544 filed Jul. 6, 2021, entitled "Orthopedic Compression Implants and Devices for Installing and Retaining the Same," which claims benefit of U.S. provisional patent application Ser. No. 63/048,269 filed Jul. 6, 2020, and entitled "Orthopedic Compression Implants," each of which is hereby incorporated herein by reference in its entirety.

STATEMENT REGARDING FEDERALLY SPONSORED RESEARCH OR DEVELOPMENT

Not applicable.

BACKGROUND

Staple-style orthopedic implants are often used to provide fixation and stability at a fracture, osteotomy or arthrodesis site to enable fusion. Some orthopedic implants are shape memory compression implants that may change dimensions as a function of temperature to offer greater fixation and stability to enable improved fusion.

BRIEF SUMMARY

Embodiments of orthopedic implants are disclosed herein. In one embodiment, a shape-memory alloy orthopedic implant comprises a bridge having a curved longitudinal axis, a first end, and a second end opposite the first end. The bridge has a radially outer surface extending axially from the first end to the second end. In addition, the shape-memory alloy orthopedic implant comprises a first leg extending from the first end of the bridge, wherein the first leg has a central axis, a fixed end fixably attached to the bridge, a free end distal the bridge, and a radially outer surface extending axially from the fixed end of the first leg to the free end of the first leg. Further, the shape-memory alloy orthopedic implant comprises a second leg extending from the second end of the bridge. The second leg has a central axis, a fixed end fixably attached to the bridge, a free end distal the bridge, and a radially outer surface extending axially from the fixed end of the second leg to the free end of the second leg. The radially outer surface of the bridge defines a first outer profile in a cross-section of the bridge taken in a plane oriented perpendicular to the longitudinal axis of the bridge. The radially outer surface of the first leg defines a second outer profile in a cross-section of the first leg taken in a plane oriented perpendicular to the central axis of the first leg. The first outer profile has a different geometry than the second outer profile.

In another embodiment, a shape-memory alloy orthopedic implant comprises a bridge having a curved longitudinal axis, a first end, a second end opposite the first end, and a radially outer surface extending axially from the first end to the second end. The radially outer surface of the bridge defines a first outer profile in a cross-section of the bridge taken in a plane oriented perpendicular to the longitudinal axis of the bridge. The first outer profile is non-rectangular. In addition, the shape-memory alloy orthopedic implant comprises a plurality of legs extending from the bridge. Each leg has a central axis disposed in a common reference plane as the curved longitudinal axis of the bridge. The radially outer surface of the bridge comprises an upper surface and a lower surface. The lower surface of the radially outer surface of the bridge is concave between the first end of the bridge and the second end of the bridge in the common reference plane in front view. The upper surface of the radially outer surface of the bridge is convex in the cross-section of the bridge taken in a plane oriented perpendicular to the longitudinal axis of the bridge.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of various exemplary embodiments, reference will now be made to the accompanying drawings in which.

DETAILED DESCRIPTION

Figure 1:
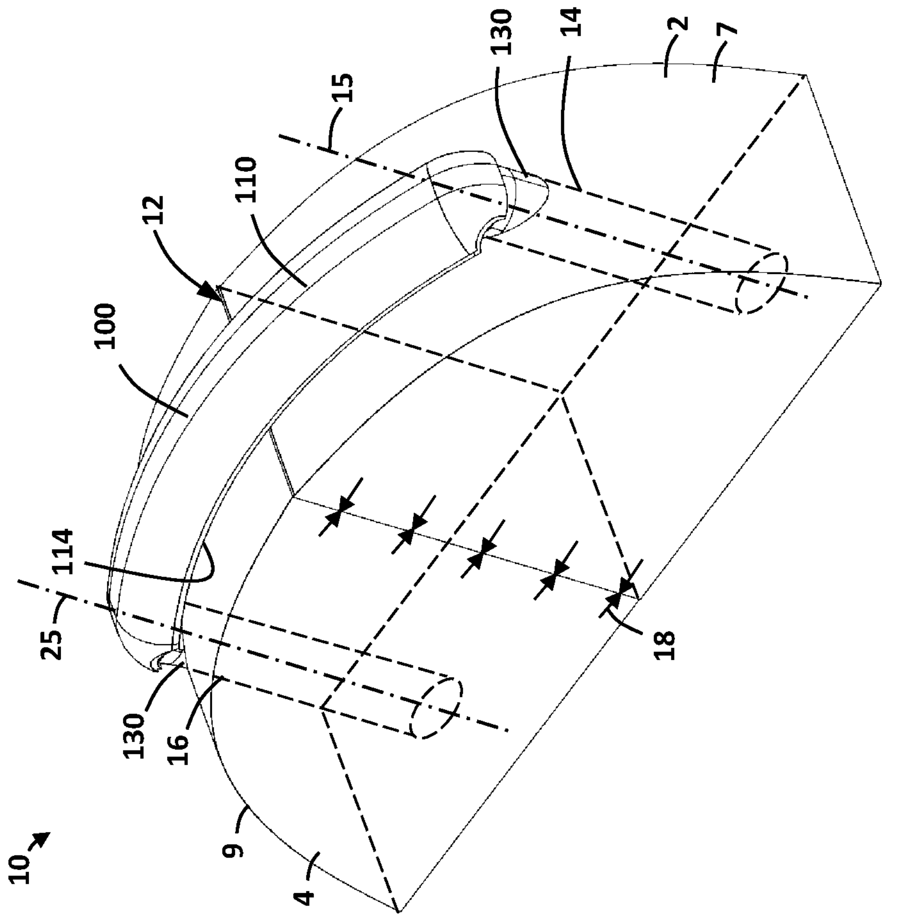
FIG. 1 is an isometric view of an embodiment of an implant for compressing two bone segments together in accordance with the principles described herein.

The following discussion is directed to various exemplary embodiments. However, one of ordinary skill in the art will understand that the examples disclosed herein have broad application, and that the discussion of any embodiment is meant only to be exemplary of that embodiment, and not intended to suggest that the scope of the disclosure, including the claims, is limited to that embodiment.

The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection of the two devices, or through an indirect connection that is established via other devices, components, nodes, and connections. In addition, as used herein, the terms "axial" and "axially" generally mean along or parallel to a given axis (e.g., central axis of a body or a port), while the terms "radial" and "radially" generally mean perpendicular to the given axis. For instance, an axial distance refers to a distance measured along or parallel to the axis, and a radial distance means a distance measured perpendicular to the axis. As used herein, the terms "approximately," "about," "substantially," and the like mean within 10% (i.e., plus or minus 10%) of the recited value. Thus, for example, a recited angle of "about 80 degrees" refers to an angle ranging from 72 degrees to 88 degrees.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

As previously described above, staple-style orthopedic implants are designed to provide fixation and stability at a fracture, osteotomy, or arthrodesis site to enable fusion. Such implants may include 2, 3, 4 or more legs. The legs of the implant are connected with a bridge that may come in various forms, sizes and shapes depending on the particular application and anatomy. The implants are often part of system that includes instruments for use with the implants and an associated surgical technique. The instruments may include for example: sizing guides/templates, drill guides, drill or drilling pins, locating pins/pull pins, tamps, insertion tools, removal tools, and possibly heat source instruments for shape memory alloys.

There are generally three types of orthopedic staple-style implants: (1) static staples, (2) mechanical compression staples, and (3) shape memory compression staples. Static staples generally represent the first-generation orthopedic bone staples. These basic, U-shaped staples are typically made from medical grade titanium or stainless-steel materials suitable for medical device application. Traditional milling, wire-EDM, or wire-bending methods are usually employed to manufacture static staples. Static staples usually provide minimal to no compression to an osteotomy or arthrodesis site, and provide minimal stability to promote fusion at the site. Mechanical compression staples are typically manufactured from stainless steel materials. These staples rely on the application of an external force to achieve compression between bone fragments at an osteotomy or arthrodesis site. In particular, by physically bending the bridge with a suitable instrument, the distance between the implant legs is shortened, thereby allowing the legs to provide compression therebetween. Due to the limited elasticity of stainless steel, the compression provided is relatively short-lived. In addition, the deformation of the bridge may cause the tips of the implant legs to splay resulting in the distraction of the bone segments. Shape memory compression staples are often made from medical grade Nitinol suitable for medical device applications. Nitinol is a metal alloy made of approximately half nickel and half titanium. Nitinol exhibits phase transformation whereby the molecular arrangement of Nitinol can vary according to the temperatures to which it is exposed. At lower temperatures, the crystalline architecture of Nitinol resembles an accordion making it relatively unstable, malleable, and weak. This is referred to as the martensitic phase of Nitinol (martensite).

At higher temperatures, the crystalline structure of Nitinol is rearranged into a cubic form making it contracted, rigid, and strong. This is referred to as the austenitic phase of Nitinol (austenite). The temperature range at which Nitinol transforms from the martensitic phase into austenitic phase can be adjusted and manipulated through manufacturing processes. During manufacturing, a Nitinol device undergoes heat treatments that "program" the temperature ranges that trigger the transition between the martensitic and austenitic phases. For example, when a Nitinol device is heated, the programing dictates the beginning of the phase transformation from martensite to austenite (Austenite Start temperature or $A_s$) and the end of the transformation (Austenite Finish temperature or $A_f$). In addition, when a Nitinol device is cooled, the programming dictates the beginning of the phase transformation from austenite to martensite (Martensite Start temperature or $M_s$) and the end of the transformation (Martensite Finish temperature or $M_f$). In addition to the aforementioned phase transformation, Nitinol exhibits shape memory and superelastic/pseudoelastic characteristics.

With regards to shape memory, a Nitinol device can be designed to transform from one shape to another when exposed to heat. For example, prior to heat treating, the Nitinol device may be cooled, and thus become malleable in the martensite material phase and shaped into a particular form that imparts internal residual stresses. Heat treatment can then be applied, which sets or "bakes" this established shape into the memory of the implant. Then, when the Nitinol device is heated through its transformation temperature range, the device will revert to its predetermined final shape as it undergoes the phase transformation to Austenite.

Compared to most other metals, Nitinol can withstand a large amount of strain, for example up to 8%, and still recover its original shape. The superelastic characteristic is displayed when a Nitinol staple is warmed through its transformation temperature range but is constrained and prevented from returning to its original shape. While constrained in a deformed shape, as is the case when a Nitinol bone staple is in bone, continuous exposure to sufficient heat allows the implant to behave like an elastic spring. This superelastic effect thus may be used to maintaining a long-term compressive force between bone segments over a large displacement range.

There are two varieties of staples are made from Nitinol: Thermally-activated and Superelastic. The transition temperature ranges of these types of implants vary and can be classified as either heat-activated or body temperature-activated. Heat-activated Nitinol bone staples have an $A_s$ and $A_f$ above body temperature. These implants are inserted into bone in the malleable martensitic phase and are exposed to an external heat via electrocautery or bi-polar electrical resistance to convert the implant from martensite to austenite, and thus, promote shape change that creates initial compression between joined bone segments. Compression is maintained through the superelastic effect as the implant is constrained in an open position by the bone segments. Body temperature-activated Nitinol bone staples have a transition temperature range that is slightly lower than body temperature. Since their austenite start temperature ($A_s$) may be at or below room temperature, these implants may utilize freezer storage to prevent premature closure. These implants are placed into the osteotomy or arthrodesis site while still in a frozen state, and then compress the joined bone segments through the shape memory effect as they warm to body temperature. Compression is again maintained through the superelastic effect as the implant is constrained in an open position by the bone segments. Both types of thermally-activated Nitinol implants (e.g., heat- and body temperature-activated) have not, however, been widely accepted. Due to manufacturing limitations of thermally-activated Nitinol, traditional machining methods (milling, grinding, turning, etc.) have generally not been cost-effective. Thus, many Nitinol staples are created using raw Nitinol wire material that is bent to the desired shape and heat treated to set the shape. This has generally limited implant geometries to simple U-shaped staples having two legs and a constant cross-section between the distal ends of the implant legs.

Superelastic shape memory compression staples are the latest generation of Nitinol bone implants. The austenite finish temperature ($A_f$) for these implants is significantly below room temperature, for example 10 to −20 degrees C, thus freezer storage to maintain an initial shape in the martensite material phase may not be sufficient, as implants may begin to deflect before being placed into the osteotomy or arthrodesis site. Thus, in some instances, external constraint devices may be used to mechanically open and constrain the legs of the implant prior to inserting them into pre-drilled holes in bone. Upon release of the constraining tool, the superelastic effect is transferred from the tool to the bone to achieve compression across the osteotomy or arthrodesis site.

Due to a relatively low $A_f$ (e.g., 10 to −20 degrees C), superelastic Nitinol implants may utilize different manufacturing approaches as compared to implants made from wire raw material, and thus, may include more configurations and geometries, such as additional staple legs. For example, starting with bulk raw material with low $A_f$, implants may be machined using wire Electrical Discharge Machining (EDM) to create the desired shapes. The shapes of these implants are however limited to the shapes that may result from the intersection of wire paths from two planes, and thus, such implants may not conform to the complex anatomies of the body. Additionally, due to the EDM manufacturing process, the leg features typically have square or rectangular cross-sectional shapes that do not match the shape and size of the round drilled holes in which the legs are installed. A result of this mismatch is that the implant leg strength may not be maximized, and thus, the most common fracture location of a staple is in the leg features. This typically limits the use of staples to applications in lower biomechanical loading areas. However, as staples become more common practice for surgeons, there is a continued desire to use staples in high biomechanical loading applications.

Accordingly, embodiments disclosed herein include staple-style implants that may be produced with more complex geometries than what is typically possible with EDM machining. In particular, some embodiments disclosed herein may utilize advanced milling techniques and or electrochemical machining (ECM) to produce implants having rounded or partially rounded legs that maximize strength within a given drilled hole. In addition, some embodiments disclosed herein may include implant bridges that have a different cross-sectional shapes than the corresponding legs. In particular, the cross-section of the bridge may include a partially rounded profile that provides a low implant profile and establishes a more anatomically conforming fit. Moreover, in some embodiments, the cross-section of the bridge and/or the cross-section of the legs are non-rectangular (e.g., elliptical, D-shaped, circular, semi-circular, or polygonal).

Referring now to FIG. 1, an embodiment of a staple-style implant 100 is shown. In this embodiment, implant 100 is a U-shaped staple used to fix, stabilize, and apply compression (illustrated with arrows 18 in FIG. 1) to a fracture 12 between a first bone segment 2 and a second bone segment 4 of a broken bone. Each bone segment 2, 4 has a curved outer surface or profile 7, 9, respectively, proximal implant 100. Bone segments 2, 4 represent an exemplary curved profile (e.g., round, elliptical, etc.) such as that of a generally cylindrical long bone (e.g., femora, tibiae, humeri, ulnae, metacarpals, clavicle, etc.), however, as will be described more fully below, implant 100 may be used with any classification of bone (e.g., short, flat, sutural, irregular, sesamoid, or long), and in locations with or without a curved profile. Although break 12 is shown generally along a plane oriented perpendicular to curved profiles 7, 9, in general, break 12 may be positioned at any angle with respect to curved profiles 7, 9.

In this embodiment, implant 100 includes a bridge 110 and a plurality of legs 130 extending from bridge 110. When secured to bone segments 2, 4, bridge 110 extends across or spans break 12, while legs 130 penetrate into corresponding bone segments 2, 4 via holes 14, 16, respectively. In particular, a first hole 14 is drilled into first bone segment 2 and a second hole 16 is drilled into second bone segment 4. First hole 14 has a linear central or longitudinal axis 15 and second hole 16 has a linear central or longitudinal axis 25 that is spaced apart from and oriented parallel to first axis 15. Legs 130 are pressed into and secured within holes 14, 16 via an interference fit, and maintain static positions relative to bone segments 2, 4, as elastic energy stored within implant 100 applies compression 18 across the break 12.

Figure 3:
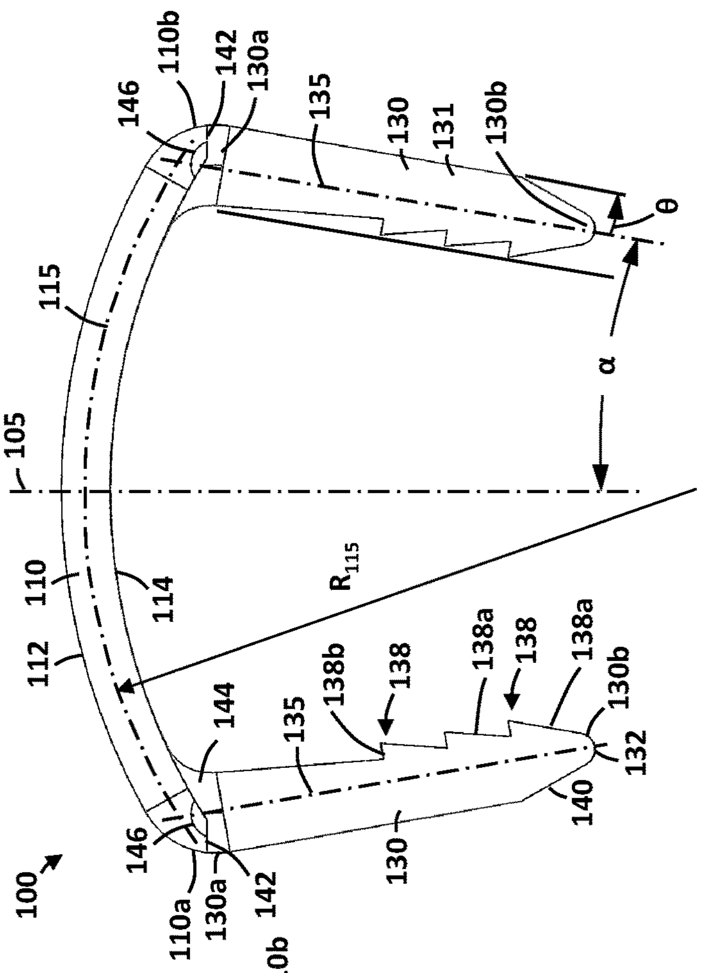
FIG. 3 is a front view of the implant of FIG. 2.
Figure 2:
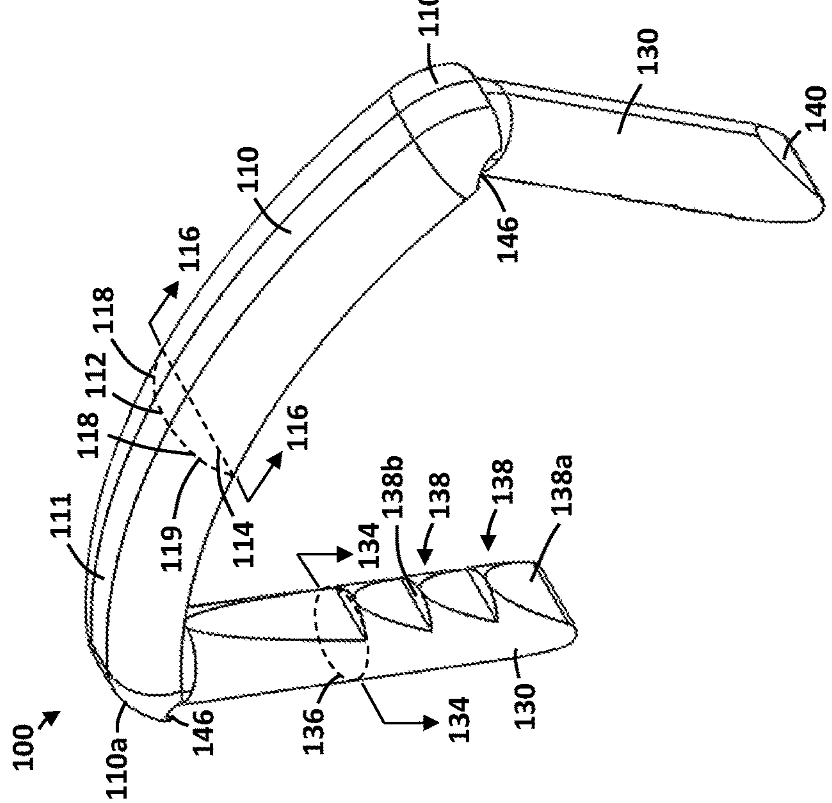
FIG. 2 is an isometric view of the implant of FIG. 1.

Referring now to FIGS. 2 and 3, implant 100 has a central axis 105 passing through the geometric center of bridge 110 and centered between legs 130 in front view (FIG. 3). In addition, bridge 110 has a curved central or longitudinal axis 115, a first terminal end 110*a*, and a second terminal end 110*b* opposite end 110*a*. Each leg 130 extends from bridge 110, and in particular, extends from a corresponding end 110*a*, 110*b* of bridge 110. Each leg 130 has a central or longitudinal axis 135 laterally spaced apart from central axis 105, a first or fixed end 130*a* fixably attached to and integral with the corresponding end 110*a*, 110*b* of bridge 110, and a second or free end 130*b* distal bridge 110. In this embodiment, each central axis 135 is linear, longitudinal axis 115 of bridge 110 intersects axes 105, 135, and axes 105, 115, 135 lie in a common plane. For purposes of clarity and further explanation, the common plane within which axes 105, 115, 135 are disposed may also be referred to herein as the "reference plane." In FIG. 3, the reference plane is a plane oriented parallel to the sheet of paper on which the drawing is shown.

As best shown in FIG. 3, each leg 130 is oriented at a leg angle $\alpha$ measured between the corresponding axis 135 and central axis 105 in the reference plane (in front view of FIG. 3). In embodiments described herein, leg angle $\alpha$ of each leg 130 ranges from about 0 degrees to about 20 degrees, alternatively ranges from about 0 degrees to about 15 degrees, and alternatively ranges from about 0 degrees to about 10 degrees. In embodiments where the leg angles $\alpha$ are greater than 0 degrees, such as that shown in FIGS. 2 and 3, second ends 130*b* of legs 130 are positioned closer to central axis 105 than first ends 130*a*, the legs 130 may be referred to herein as "inwardly biased." Thus, in some embodiments, linear central axis 135 of the first leg 130 is not parallel to linear central axis 135 of the second leg 130. In general, the leg angles $\alpha$ of the legs 130 may be the same or different. In this embodiment, each leg angle $\alpha$ is an acute angle between 0 degrees and 10 degrees, legs 130 are inwardly biased, and each leg angle $\alpha$ is the same.

Referring now to FIG. 3, as previously described, central axis 115 of bridge 110 is curved. In general, the central axis 115 may have a constant or variable radius of curvature $R_{115}$ measured in the reference plane in front view (FIG. 3) from a point along central axis 105 to central axis 115 of bridge 110. In embodiments described herein, the radius of curvature $R_{115}$ of central axis 115 at any point along central axis 115 can range from about 0 mm (i.e., linear) to about 200 mm, alternatively range from about 15 mm to about 50 mm, and more alternatively range from about 20 mm to about 30 mm. It should be appreciated that the radius of curvature $R_{115}$ of central axis 115 can vary along its length between ends 110*a*, 110*b* or be constant along its length between ends 110*a*, 110*b*.

Referring again to FIGS. 2 and 3, each leg 130 has a radially outer surface 131 extending axially (relative to corresponding axis 135) between ends 130*a*, 130*b*, a plurality of axially spaced serrations 138 disposed along outer surface 131, and a bevel 140 disposed along outer surface 131 at end 130*b*.

As best shown in FIG. 2, each leg 130 has a cross-section 134 taken in a plane oriented perpendicular to the corresponding axis 135. In cross-section 134, outer surface 131 defines a non-rectangular outer shape or profile 136. In this embodiment, outer surface 131 of each leg 130 is a cylindrical surface extending axially (relative to corresponding axis 135) from end 130*a* to end 130*b*, and thus, profile 136 at cross-section 134 is circular (FIG. 2). As described in more detail below, in some applications, the cylindrical shapes of the legs of an implant (e.g., cylindrical radial outer surface 131 of legs 130) may be advantageous as the cylindrical geometry can more fully fill the drilled hole (as shown in FIG. 1 at holes 14, 16), as compared to a rectangular prismatic geometry, and thus, offers the potential for enhanced bending strength and fixation within the bone segments (e.g., bone segments 2, 4). More specifically, rectangular cross-sectional dimensions of legs having a rectangular prismatic shape are limited as the sharp corners of the cross-section contact the cylindrical inner surface of the bone defined by the drilled hole, and any increases in one of the cross-sectional dimensions of the rectangular cross-section may result in sufficient interference between the legs and bone segments to restrict insertion of the legs into the bone segments.

Although legs 130 have cylindrical outer surfaces 131 defining circular profiles 136 in cross-sections 134 taken perpendicular to axes 135 in this embodiment, in other embodiments, the legs (e.g., legs 130) may have outer surfaces with other geometries that define other non-rectangular profiles (e.g., profiles 136) in cross-sections taken perpendicular to the central axes of the legs (e.g., such as polygons, semi-circular, elliptical, etc. along section 134).

In this embodiment, outer surface 131 of each leg 130 is cylindrical, and thus, a leg taper angle $\theta$ measured from central axis 135 to outer surface 131 of each leg 130 in the reference plane in front view (FIG. 3) is zero at all points along the axis 135. However, in other embodiments, the outer surface of each leg (e.g., outer surface 131 of each leg 130) is frustoconical and characterized by a non-zero leg taper angle $\theta$. In embodiments described herein, leg taper angle $\theta$ ranges from 0 degrees to about 2.5 degrees, alternatively ranges from about 0.075 degrees to about 1.5 degrees, and alternatively ranges from about 0.125 degrees to about 1.25 degrees. In some applications, a non-zero taper angle $\theta$ may be advantageously facilitate a wedging fit between the legs and a cylindrically shaped drilled hole, which may enhance the retention of the implant with the bone segments. In addition, non-zero taper angles θ may allow a narrower tip (e.g., tip 132), which may aid in insertion of the leg into holes 14, 16 (as shown in FIG. 1), while allowing an increased diameter at the fixed ends of the legs to increase the bending strength at the joints between the legs and the bridge (e.g., bridge 110).

Referring still to FIGS. 2 and 3, serrations 138 are axially spaced (relative to corresponding axis 135) between ends 130*a*, 130*b* and provided along outer surface 131 on the inside of each leg 130 (i.e., along the sides of legs 130 that face toward each other and axis 105). In this embodiment, each serration 138 is defined by a planar sloped surface 138*a* that slopes radially inward toward the corresponding axis 135 moving axially toward end 130*b* of the corresponding leg 130, and an upward facing planar shoulder 138*b* extending radially inward from the sloped surface toward axis 135 of the corresponding leg 130. One bevel 140 is provided along outer surface 131 on the outside of each leg 130 (i.e., along the sides of legs 130 that face away from each other and axis 105), and extends from end 130*b* of each leg 130. Bevel 140 is a planar surface. The planar sloped surface 138*a* on the inside of each leg 130 at end 130*b* and the bevel 140 on the outside of each leg 130 define tapered tips 132 at ends 130*b* of legs 130.

As best shown in FIG. 2, bridge 110 has a radially outer surface 111 extending axially (relative to axis 115) from end 110*a* to end 110*b*. In addition, bridge 110 has a cross-section 116 taken in a plane oriented perpendicular to axis 115. In cross-section 116, outer surface 111 of bridge 110 defines a non-rectangular outer shape or profile 119. In this embodiment, profile 119 at cross-section 116 is generally D-shaped. In particular, outer surface 111 includes a first or upper surface 112, a second or lower surface 114, and a pair of fillet or lateral surfaces 118 extending from upper surface 112 to lower surface 114. Upper surface 112 and lower surface 114 are oriented parallel to each other and central axis 115 in the front view (FIG. 3). As previously described, axis 115 is curved, and thus, upper surface 112 is a convex surface, whereas lower surface 114 is a concave surface. In a cross-section of bridge 110 taken in a plane oriented perpendicular to axis 115 (e.g., section 116), bridge 110 has an outer profile defined by outer surface 111 that is flat along upper surface 112 and flat along lower surface 114. Fillets 118 are curved, convex surfaces extending axially from end 110*a* to end 110*b*. Although the outer profile of bridge 110 defined by outer surface 111 that is flat along upper surface 112 and flat along lower surface 114 in a cross-section taken in a plan oriented perpendicular to axis 115, in other embodiments, the distinct upper surface (e.g., upper surface 112) is eliminated such that the fillets (e.g., fillets 118) meet at the top of the bridge, and in yet other embodiments, the lower surface (e.g., lower surface 114) may include a concavity, fillet, or notch that extends inward towards the central axis of the bridge (e.g., towards central axis 115).

Although bridge 110 has an outer surface 111 defining D-shaped profiles 119 in cross-sections 116 taken perpendicular to axis 115 in this embodiment, in other embodiments, the bridge (e.g., bridge 110) may have an outer surface with a geometry that defines other non-rectangular profiles (e.g., profiles 119) in cross-sections taken perpendicular to the central axes of the bridge (e.g., such as polygonal, semi-circular, elliptical, circular, etc.). In addition, the non-rectangular profile of the legs (e.g., legs 130) in cross-sections taken perpendicular to the central axes of the legs may be the same or different from the non-rectangular profile of the bridge in cross-sections taken perpendicular to the central axis of the bridge. For example, as previously described, in this embodiment, each leg 130 has a circular profile 136 in cross-sections 134 taken in planes oriented perpendicular to axes 135 and bridge 110 has a D-shaped profile 119 in cross-sections 116 taken in a plane perpendicular to axis 115.

In this embodiment, the cross-sectional area of the bridge 110 in any plane oriented perpendicular to axis 115 (e.g., section 116) is equal to or greater than the cross-sectional area of each leg 130 taken in any plane oriented perpendicular to axis 135 (e.g., section 134). In embodiments described herein, the ratio of (i) the cross-sectional area of the bridge (e.g., bridge 110) in any plane oriented perpendicular to the central axis of the bridge (e.g., axis 115) to (ii) the cross-sectional area of each leg (e.g., leg 130) in any plane oriented perpendicular to the central axis of the leg (e.g., axis 135) is 1.0 to 10.0, alternatively about 1.5 to 3.0, and alternatively about 1.5 to 2.0.

As described further below, in some applications, the D-shaped cross-section of bridge 110 and the radius of curvature $R_{115}$ between ends 110*a*, 110*b* in the reference plane provide a conforming fit along the generally convex, cylindrical outer surface of a bone (as shown in FIG. 1). Without being limited to this or any other theory, the lower surface 114 defining a generally flat profile in cross-sectional view in a plane oriented perpendicular to axis 115 may reduce the height to which the implant 100 extends from the bone segments 2, 4, while the upper surface 112 having a generally curved convex profile in cross-sectional view in a plane oriented perpendicular to axis 115 may provide a smooth, gradual transition to minimizes irritation of soft tissue adjacent the bone.

Referring again to FIGS. 2 and 3, as described above, legs 130 and bridge 110 have different cross-sectional geometries. To smoothly blend legs 130 and bridge 110 where fixed ends 130*a* of legs 130 meet lower surface 114 of bridge 110, in this embodiment, implant 100 includes smoothly curved concave transition surfaces 144 between fixed ends 130*a* and lower surface 114. Adjacent transition surfaces 144 and proximal ends 130*a* of legs 130, the portion of each end 110*a*, 110*b* of bridge 110 that extends laterally (relative to the reference plane) beyond legs 130 along lower surface 114 includes a pair of laterally opposed, downward facing planar shoulders 142 and a pair of laterally opposed, downward facing concave cavities or recesses 146. In this embodiment, shoulders 142 are oriented perpendicular to the reference plane and recesses 146 have semi-cylindrical geometries. As will be described in more detail below, shoulders 142 and/or recesses 146 are sized and positioned to mate and engage with a device for manipulating, inserting, or positioning implant 100. Accordingly, shoulders 142 and recesses 146 may also be described as tool engagement shoulders 142 and tool engagement recesses 146, respectively.

At each end 110*a*, 110*b*, the pair of shoulders 142 and the pair of recesses 146 are disposed on opposite sides of axis 115 and the reference plane. Thus, it should be appreciated that although only two shoulders 142 and two recesses 146 are shown in the front view of FIG. 3, four shoulders 142 and four recesses 146 are included as implant 100 is symmetric about the reference plane, and thus, two additional shoulders 142 and two additional recesses 146 are included along the opposite side of implant 100. Shoulders 142 and recesses 146 may be useful in reducing bending stress concentrations and may be used to grip implant 100 with a surgical insertion or retaining tool. In particular, and as will be described in more detail below, forces may be applied to implant 100 at shoulders 142 and/or recesses 146 to restrain or impart bending moments into bridge 110.

In this embodiment, implant 100 is made of a Nitinol material, and thus, can be heat treated and programed, as discussed above, to have shape memory and superelastic/pseudoelastic characteristics such that implant 100 may be classified as a superelastic shape memory implant, and may transform from one shape to another when exposed to heat.

Referring now to FIGS. 1-3, the surgical use of implant 100 may utilize the shape memory characteristics of Nitinol to impart compressive loads across a fracture, osteotomy, or arthrodesis site (e.g., compression 18 across break 12 as shown in FIG. 1) to enable fusion. In the manner previously described, implant 100 can be made of Nitinol and programed though deformation and heat treatment, such that the shape memory of the Nitinol material increases leg angle α (e.g. ends 130*b* move inward toward axis 105) and/or translates ends 110*a*, 110*b* of bridge 110 towards central axis 105 in response to heating of implant 100. Such heating of implant 100 may be accomplished with an external source (e.g., heat-activated), or as implant 100 is brought to room temperature or body temperature (e.g., body temperature-activated). In addition, in some embodiments, the shape transformation may have already occurred and an external tool may be used to restrain the deformation of implant 100. For example, in some embodiments, the external tool may engage with a plurality of shoulders 142 and/or with a plurality of recesses 146, and apply forces to bridge 110 to elastically flex bridge 110 at ends 110*a*, 110*b* to bring axes 135 into parallel with central axis 105 to reduce each leg angle α. Thus, in some embodiments, legs 130 may be constrained with axes 135 oriented parallel and coaxially aligned with central axes 15, 25 of holes 14, 16 in bone segments 2, 4, respectively (as shown in FIG. 1), and then inserted into corresponding holes 14, 16. Legs 130 are advanced into holes 14, 16 until lower surface 114 of bridge 110 is pressed into contact (or approximate contact) with bone segments 2, 4, as the curvature of bridge 110 may be specifically designed and selected to accommodate the underlying curved profiles 7, 9 of bone segments 2, 4 to allow a low implant profile and establish an anatomically conforming fit. Next, the external tool may be removed, to release the strain energy of the elastically deformed implant 100 and allow legs 130 to apply compression across break 12 as the free ends 130*b* of legs and/or ends 110*a*, 110*b* of bridge 110 are biased inward toward central axis 105.

Figure 5:
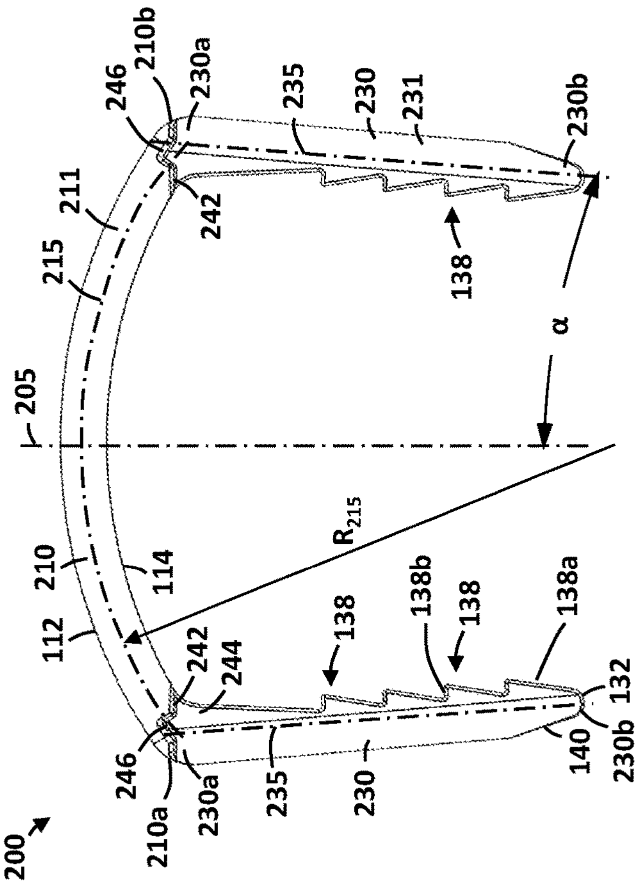
FIG. 5 is a front view of the implant of FIG. 4.
Figure 4:
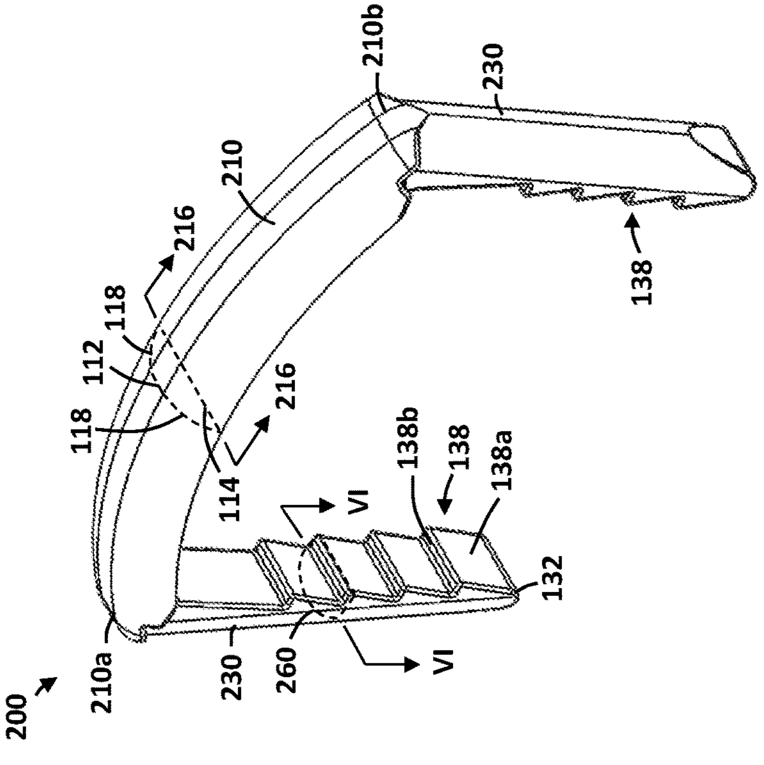
FIG. 4 is an isometric view of an embodiment of an implant for compressing two bone segments together in accordance with the principles described herein.

Referring now to FIGS. 4 and 5, an embodiment of a staple-style implant 200 is shown. In general, implant 200 can be used in place of implant 100 previously described and shown in FIG. 1. Implant 200 is substantially the same as implant 100 previously described above, and thus, features of implant 200 that are the same as and shared with implant 100 are identified with the same reference numerals, and the discussion below will focus on the features of implant 200 that are different from implant 100.

Similar to implant 100 previously described, implant 200 is a U-shaped staple including a bridge 210 and a plurality of legs 230 extending from bridge 210. Implant 200 has a central axis 205 passing through the geometric center of bridge 210 and centered between legs 230 in front view (FIG. 5). In addition, bridge 210 has a curved central or longitudinal axis 215, a first terminal end 210*a*, and a second terminal end 210*b* opposite end 210*a*. Each leg 230 extends from bridge 210, and in particular, extends from a corresponding end 210*a*, 210*b* of bridge 210. Each leg 230 has a central or longitudinal axis 235 laterally spaced apart from central axis 205, a first or fixed end 230*a* fixably attached to and integral with the corresponding end 210*a*, 210*b* of bridge 210, and a second or free end 230*b* distal bridge 210. In this embodiment, each central axis 235 is linear, longitudinal axis 215 of bridge 210 intersects axes 205, 235, and axes 205, 215, 235 lie in a common plane. For purposes of clarity and further explanation, the common plane within which axes 205, 215, 235 are disposed may also be referred to herein as the "reference plane." In FIG. 5, the reference plane is a plane oriented parallel to the sheet of paper on which the drawing is shown.

As best shown in FIG. 5, each leg 230 is oriented at a leg angle α measured between the corresponding axis 235 and central axis 205 in the reference plane (in front view of FIG. 5). Leg angles α may be the same as previously described with respect to implant 100. In this embodiment, each leg angle α is the same.

Referring still to FIG. 5, as previously described, central axis 215 of bridge 210 is curved. Similar to central axis 115 of bridge 110 previously described, the central axis 215 may have a constant or variable radius of curvature $R_{215}$ measured in the reference plane in front view (FIG. 5) from a point along central axis 205 to central axis 215 of bridge 210. The radius of curvature $R_{215}$ may be the same as previously described with respect to radius of curvature $R_{115}$ of central axis 115.

Referring again to FIGS. 4 and 5, each leg 230 has a radially outer surface 231 extending axially (relative to corresponding axis 235) between ends 230*a*, 230*b*, a plurality of axially spaced serrations 138 disposed along outer surface 231, and a bevel 140 disposed along outer surface 231 at end 230*b*. Serrations 138 and bevel 140 are as previously described with respect to implant 100. The planar sloped surface 138*a* on the inside of each leg 230 at end 230*b* and the bevel 140 on the outside of each leg 230 define tapered tips 132 at ends 230*b* of legs 230.

Unlike legs 130 previously described, which have a cylindrical outer surface 131, in this embodiment, outer surface 231 of each leg 230 includes a semi-cylindrical surface disposed about axis 235 and extending axially from end 230*a* to end 230*b*. In particular, as illustrated by the D-shaped profile 260 of a cross-section of one leg 230 taken in a plane oriented perpendicular to axis 235, outer surface 231 includes a semi-cylindrical surface 262, a planar flat 266, and a pair of planar side surfaces 264 extend from surface 262 to flat 266. Semi-cylindrical surfaces 262 are provided along outer surface 231 on the outside of legs 230 (i.e., along the sides of legs 230 that face away from each other and axis 205), while planar flats 266 are provided along outer surface 231 on the inside of legs 230 (i.e., along the sides of legs 230 that face each other and axis 205). Semi-cylindrical surfaces 262 and side surfaces 264 extends axially from corresponding end 230*a* to corresponding end 230*b*, however, in D-shaped profile 260, flat 266 is defined by one of the serrations 138.

Figure 6:
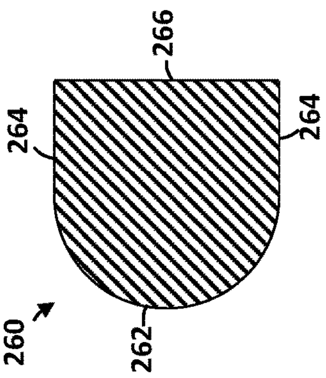
FIG. 6 is a cross-sectional view of one of the legs of the implant of FIG. 4 taken in section VI-VI of FIG. 4.

For similar reasons as previously described, in some surgical applications, the semi-cylindrical shape and geometry of legs 230 may be advantageous, as it may enable close mating and conforming contact with a substantial portion of the inner cylindrical surface of a drilled hole (e.g., as shown in FIG. 1 at holes 14, 16), as compared to a rectangular prismatic shape. In addition, non-cylindrical features of profile 260 (e.g., flat 266 and side surfaces 264) may be configured to provide an interference fit along portions of serrations 238, which may increase the retention (herein also referred to as "bite") with portions of the bone engaged by serrations 238. Accordingly, an increased thickness of legs 230 may be achieved, which offers the potential to increase the bending strength and stiffness of legs 230 as compared to a rectangular cross-section and increase the loads during deformation without damaging legs 230 at the connections with bridge 210. The angle between edges 264 and inner flat 266 may be varied to increase or decrease the interference fit or bite with a cylindrically drilled hole (as shown in FIG. 1 at holes 14, 16), and in some embodiments (such as the embodiment of FIG. 6), side surfaces 264 may be parallel to one another, and thus, may intersect inner flat 266 at approximately ninety degrees.

Referring again to FIGS. 4 and 5, bridge 210 may have the same or similar geometry as bridge 110 previously described. For example, as shown at section 216 of FIG. 4, bridge 210 has a D-shaped cross-section in a plane oriented perpendicular to axis 215, which may again provide a conforming fit along the convex cylindrical outer surface of a bone (as shown in FIG. 1). Similar to implant 100, to smoothly blend legs 230 and bridge 210 where fixed ends 230*a* of legs 230 meet lower surface 114 of bridge 210, in this embodiment, implant 200 includes smoothly curved concave transition surfaces 244 between fixed ends 230*a* and lower surface 114. Adjacent transition surfaces 244 and proximal ends 230*a* of legs 230, the portion of each end 210*a*, 210*b* of bridge 210 that extends laterally (relative to the reference plane) beyond legs 230 along lower surface 114 includes a pair of laterally opposed, downward facing planar shoulders 242 and a pair of laterally opposed, downward facing concave cavities or recesses 246. In this embodiment, shoulders 242 are oriented perpendicular to the reference plane and recesses 246 have triangular geometries. Shoulders 242 and/or recesses 246 are sized and positioned to mate and engage with a device for manipulating, inserting, or positioning implant 200. Accordingly, shoulders 242 and recesses 246 may also be described as tool engagement shoulders 242 and tool engagement recesses 246, respectively.

At each end 210*a*, 210*b*, the pair of shoulders 242 and the pair of recesses 246 are disposed on opposite sides of axis 215 and the reference plane. Thus, it should be appreciated that although only two shoulders 242 and two recesses 246 are shown in the front view of FIG. 5, four shoulders 242 and four recesses 246 are included as implant 200 is symmetric about the reference plane, and thus, two additional shoulders 242 and two additional recesses 246 are included along the opposite side of implant 200. Shoulders 242 and recesses 246 may be useful in reducing bending stress concentrations and may be used to grip implant 200 with a surgical insertion or retaining tool. In particular, forces may be applied to implant 200 at shoulders 242 and/or recesses 246 to restrain or impart bending moments into bridge 210.

In this embodiment, implant 200 is made of a Nitinol material, and thus, can be heat treated and programed, as discussed above, to have shape memory and superelastic/pseudoelastic characteristics such that implant 200 may be classified as a superelastic shape memory implant, and may transform from one shape to another when exposed to heat.

Figure 7:
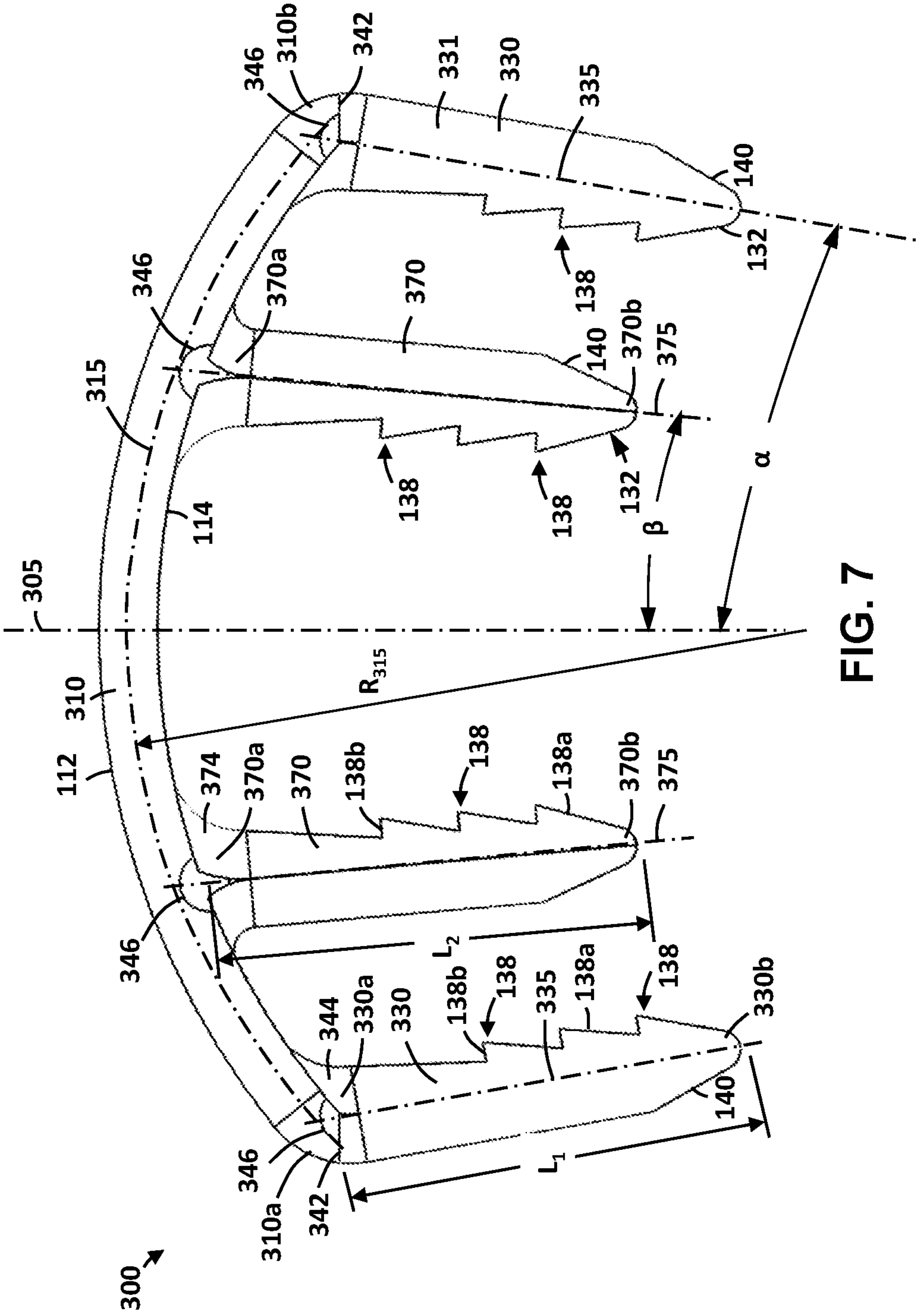
FIG. 7 is a front view of an embodiment of an implant for compressing two bone segments together in accordance with the principles described herein.

Referring now to FIG. 7, an embodiment of a staple-style implant 300 is shown. In general, implant 300 can be used in place of implant 100 previously described and shown in FIG. 1. Implant 300 is generally the same as implants 100, 200 previously described above, and thus, features of implant 300 that are the same as and shared with implants 100, 200 are identified with the same reference numerals, and the discussion below will focus on the features of implant 300 that are different from implants 100, 200.

Similar to implant 100 previously described, implant 300 is a U-shaped staple including a bridge 310 and a plurality of legs 330 extending from bridge 310. Implant 300 has a central axis 305 passing through the geometric center of bridge 310 and centered between legs 330 in front view (FIG. 7). In addition, bridge 310 has a curved central or longitudinal axis 315, a first terminal end 310*a*, and a second terminal end 310*b* opposite end 310*a*. Each leg 330 extends from bridge 310, and in particular, extends from a corresponding end 310*a*, 310*b* of bridge 310. Each leg 330 has a central or longitudinal axis 335 laterally spaced apart from central axis 305, a first or fixed end 330*a* fixably attached to and integral with the corresponding end 310*a*, 310*b* of bridge 310, and a second or free end 330*b* distal bridge 310. In this embodiment, each central axis 335 is linear, longitudinal axis 315 of bridge 310 intersects axes 305, 335, and axes 305, 315, 335 lie in a common plane. For purposes of clarity and further explanation, the common plane within which axes 305, 315, 335 are disposed may also be referred to herein as the "reference plane." In FIG. 7, the reference plane is a plane oriented parallel to the sheet of paper on which the drawing is shown.

Each leg 330 is oriented at a leg angle α measured between the corresponding axis 335 and central axis 305 in the reference plane (in the front view of FIG. 7). In this embodiment, each leg angle α is the same. Leg angles α may be the same as previously described with respect to implant 100. In some embodiments, the leg angle α of each leg 330 ranges from about 0 degrees to about 15 degrees, alternatively ranges from about 0 degrees to about 10 degrees, and alternatively ranges from about 0 degrees to about 5 degrees.

Referring still to FIG. 7, as previously described, central axis 315 of bridge 310 is curved. Similar to central axis 115 of bridge 110 previously described, the central axis 315 may have a constant or variable radius of curvature $R_{315}$ measured in the reference plane in front view (FIG. 7) from a point along central axis 305 to central axis 315 of bridge 310. The radius of curvature $R_{315}$ may be the same as previously described with respect to radius of curvature $R_{115}$ of central axis 115.

Unlike implants 100, 200 previously described, in this embodiment, implant 300 includes a pair of additional legs 370 that extend from bridge 310 between legs 330, and in particular, each leg 370 extends from bridge 310 at a position between central axis 305 and one of legs 330. As legs 330 are positioned at the ends 310*a*, 310*b* of implant 300, and hence, distal from central axis 305 whereas legs 370 are positioned between axis 305 and legs 330, legs 330 may also be referred to herein as "outer legs" and legs 370 may also be referred to herein as "inner legs." Each inner leg 370 has a central or longitudinal axis 375 laterally spaced from central axis 305, a first or fixed end 370*a* fixably attached to and integral with bridge 310, and a second or free end 370*b* distal bridge 310. In this embodiment, each central axis 375 is linear, longitudinal axis 315 of bridge 310 intersects axes 375, and axes 375 lie in the reference plane.

Referring still to FIG. 7, each inner leg 370 is oriented at a leg angle β measured between the corresponding central axis 375 and central axis 305 in the reference plane. In this embodiment, each leg angle β is the same. Leg angles β may be the same as leg angles α previously described with respect to implant 100. Similar to implants 100, 200, outer legs 330 and inner legs 370 may be angled inwards toward central axis 305 such that second ends 330*b*, 370*b* of legs 330, 370, respectively, are positioned closer to central axis 305 than first ends 330*a*, 370*a*, respectively.

Each outer leg 330 has a length $L_1$ measured axially (relative to axis 335) from first end 330*a* to second end 330*b*, and each inner leg 370 has a length $L_2$ measured axially (relative to axis 375) from first end 370*a* to second end 370*b*. Lengths $L_1$ of legs 330 may be the same or different, lengths $L_2$ of legs 370 may be the same or different, and lengths $L_1$ and $L_2$ of legs 330, 370 may be the same or different. In this embodiment, the length of $L_1$ of each leg 330 and the length $L_2$ of each leg 370 is the same.

Each leg 330 has a radially outer surface 331 extending axially (relative to corresponding axis 335) between ends 330*a*, 330*b*, a plurality of axially spaced serrations 138 disposed along outer surface 331, and a bevel 140 disposed along outer surface 331 at end 330*b*. Serrations 138 are disposed along the inside of each leg 330 (relative to central axis 305), and bevel 140 is disposed on the outside of each leg 330 (relative to central axis 305). Serrations 138 and bevel 140 are as previously described with respect to implant 100. The planar sloped surface 138*a* on the inside of each leg 330 at end 330*b* and the bevel 140 on the outside of each leg 330 define tapered tips 132 at ends 330*b* of legs 330.

Each leg 370 has a radially outer surface 371 extending axially (relative to corresponding axis 375) between ends 370*a*, 370*b*, a plurality of axially spaced serrations 138 disposed along outer surface 371, and a bevel 140 disposed along outer surface 331 at end 370*b*. Serrations 138 are disposed along the inside of each leg 370 (relative to central axis 305), and bevel 140 is disposed on the outside of each leg 370 (relative to central axis 305). Serrations 138 and bevel 140 are as previously described with respect to implant 100. The planar sloped surface 138*a* on the inside of each leg 370 at end 370*b* and the bevel 140 on the outside of each leg 370 define tapered tips 132 at ends 370*b* of legs 370.

The shape and geometry of outer surfaces 331, 371 of legs 330, 370, respectively, may be different to accommodate the particular surgical implementation. In the embodiment of FIG. 7, outer surface 331 of each outer leg 330 is cylindrical, and thus, each outer leg 330 has a circular cross-section (e.g., similar to profile 136 of section 134 in FIG. 2), while outer surface 371 of each inner leg 370 has a D-shaped cross-section including a semi-cylindrical portion and a planar portion (e.g., as illustrated by profile 260 of section 6 in FIGS. 4 and 6).

Bridge 310 has the same or similar geometry as bridge 110 previously described. For example, bridge 310 has a D-shaped cross-section in a plane oriented perpendicular to axis 315, which provides a conforming fit along the cylindrical outer surface of a bone (e.g., as shown in FIG. 1). Similar to implant 100, implant 300 includes smooth concave transition surfaces 344, 374 that blend ends 330*a*, 370*a* of legs 330, 370, respectively, and lower surface 114 of bridge 310. Adjacent transition surfaces 344 and proximal ends 330*a* of legs 330, the portions of bridge 310 at ends 310*a*, 310*b* that extend laterally (relative to the reference plane) beyond legs 330 along lower surface 114 include a pair of laterally opposed, downward facing planar shoulders 342 and a pair of laterally opposed, downward facing concave cavities or recesses 346. In addition, adjacent transition surfaces 347 and proximal ends 370*a* of legs 370, the portions of bridge 310 that extends laterally (relative to the reference plane) beyond legs 370 include a pair of laterally opposed, downward facing concave cavities or recesses 346. In this embodiment, shoulders 342 are oriented perpendicular to the reference plane and recesses 346 have triangular geometries. Shoulders 342 and/or recesses 346 are sized and positioned to mate and engage with a device for manipulating, inserting, or positioning implant 300. Accordingly, shoulders 342 and recesses 346 may also be described as tool engagement shoulders 342 and tool engagement recesses 346, respectively.

At each end 310*a*, 310*b*, the pair of shoulders 342 and the pair of recesses 346 are disposed on opposite sides of axis 315 and the reference plane; and proximal transition surfaces 374, the pair of recesses 346 are disposed on opposite sides of axis 315 and the reference plane. Thus, it should be appreciated that although only two shoulders 342 and four recesses 346 are shown in the front view of FIG. 7, four shoulders 342 and eight recesses 346 are included as implant 300 is symmetric about the reference plane, and thus, two additional shoulders 342 and four additional recesses 346 are included along the opposite side of implant 300. Shoulders 342 and recesses 346 may be useful in reducing bending stress concentrations and may be used to grip implant 300 with a surgical insertion or retaining tool. In particular, forces may be applied to implant 300 at shoulders 342 and/or recesses 346 to restrain or impart bending moments into bridge 310.

In this embodiment, implant 300 is made of a Nitinol material, and thus, can be heat treated and programed, as discussed above, to have shape memory and superelastic/pseudoelastic characteristics such that implant 300 may be classified as a superelastic shape memory implant, and may transform from one shape to another when exposed to heat.

Figure 8:
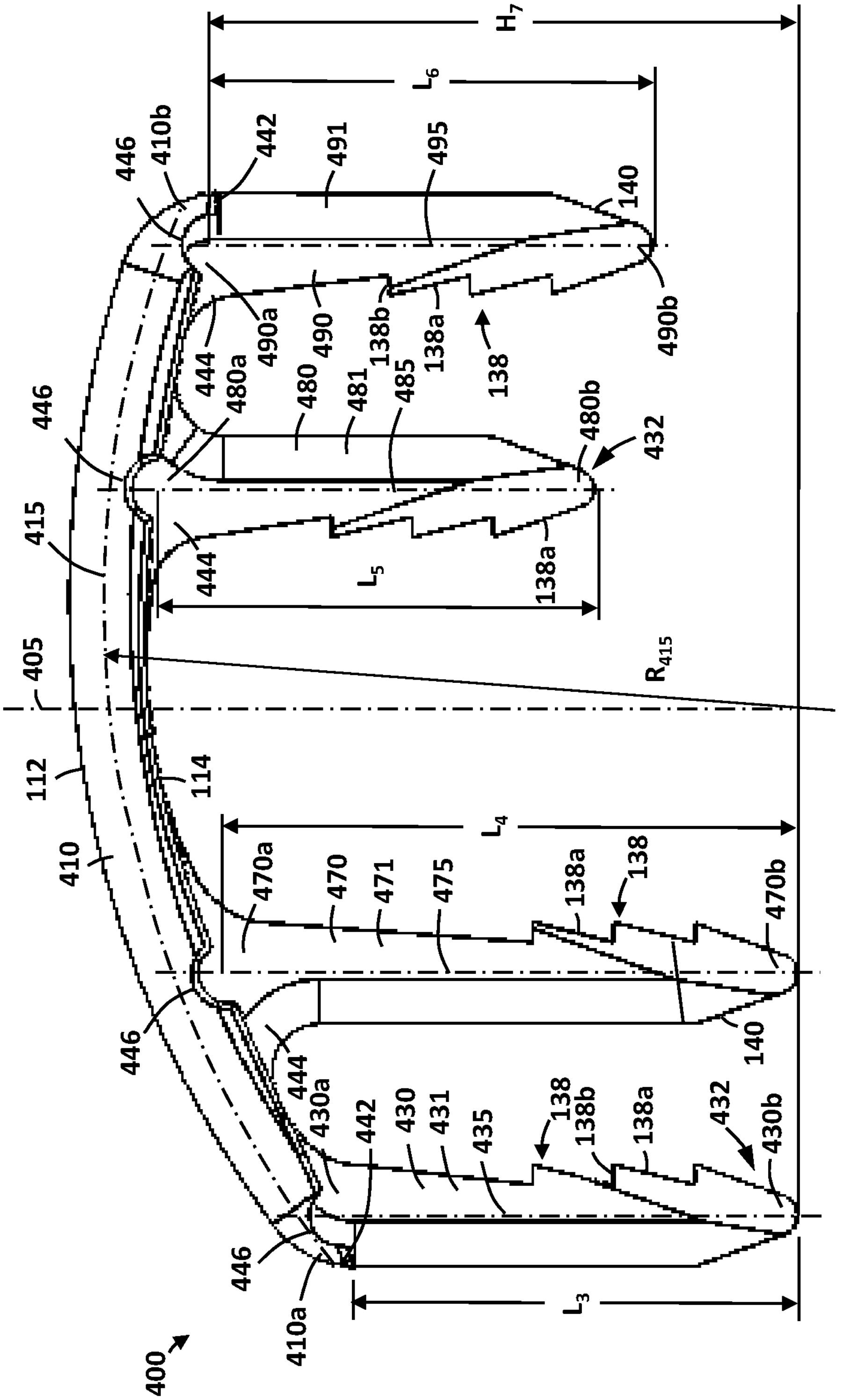
FIG. 8 is a front view of an embodiment of implant for compressing two bone segments together in accordance with the principles described herein.

Referring now to FIG. 8, an embodiment of a staple-style implant 400 is shown. In general, implant 400 can be used in place of implant 100 previously described and shown in FIG. 1. Implant 400 is similar to implant 300 previously described, and thus, features of implant 400 that are the same as and shared with implant 300 are identified with the same reference numerals, and the discussion below will focus on the features of implant 400 that are different from implant 300.

Similar to implant 300 previously described, implant 400 is a U-shaped staple including a bridge 410 and a plurality of legs 430, 470, 480, 490 extending from bridge 410. Implant 400 has a central axis 405 passing through the geometric center of bridge 410 and centered between legs 430, 490 in front view (FIG. 8). In addition, bridge 410 has a curved central or longitudinal axis 415, a first terminal end 410*a*, and a second terminal end 410*b* opposite end 410*a*. Each leg 430, 470, 480, 490 extends from bridge 410, and in particular, each leg 430, 490 extends from a corresponding end 410*a*, 410*b* of bridge 410, leg 470 extends from bridge 410 between central axis 405 and leg 430, and leg 480 extends from bridge 410 between central axis 504 and leg 490. Thus, legs 470, 480 are axially positioned (relative to longitudinal axis 415) between legs 430, 490. Accordingly, legs 470, 480 may also be referred to herein as "inner legs" and legs 430, 490 may also be referred to herein as "outer legs." Each leg 430, 470, 480, 490 has a central or longitudinal axis 435, 475, 485, 495, respectively, laterally spaced apart from central axis 305, a first or fixed end 430*a*, 470*a*, 480*a*, 490*a*, respectively, fixably attached to and integral with bridge 410, and a second or free end 430*b*, 470*b*, 480*b*, 490*b*, respectively, distal bridge 410. In this embodiment, each central axis 435, 475, 485, 495 is linear, longitudinal axis 415 of bridge 410 intersects axes 405, 435, 475, 485, 495, and axes 405, 415, 435, 475, 485, 495 lie in a common plane. For purposes of clarity and further explanation, the common plane within which axes 405, 415, 435, 475, 485, 495 are disposed may also be referred to herein as the "reference plane." In this embodiment, each axis 435, 475, 485, 495 is oriented parallel to central axis 405, however, in other embodiments, the central axis of one or more of the legs (e.g., central axis 435, 475, 485, 495) be oriented at an acute leg angle (e.g., leg angles α, β) relative to the central axis of the implant (e.g., central axis 405) as previously described with respect to implant 300.

Referring still to FIG. 8, each leg 430, 470, 480, 490 has a length $L_3$, $L_4$, $L_5$, $L_6$, respectively, measured axially (relative to axis 435, 475, 485, 495, respectively) from first end 430*a*, 470*a*, 480*a*, 490*a*, respectively, to second end 430*b*, 470*b*, 480*b*, 490*b*, respectively. In general, the lengths $L_3$, $L_4$, $L_5$, $L_6$ of legs 430, 470, 480, 490 may be the same or the lengths $L_3$, $L_4$, $L_5$, $L_6$, of two or more legs 430, 470, 480, 490 may be different. In this embodiment, the length $L_3$, $L_4$, $L_5$, $L_6$ of each leg 430, 470, 480, 490 is different.

Each leg 430, 470, 480, 490 has a radially outer surface 431, 471, 481, 491, respectively, extending axially (relative to the corresponding central axis 435, 475, 485, 495) between first end 430*a*, 470*a*, 480*a*, 490*a*, respectively, and second end 430*b*, 470*b*, 480*b*, 490*b*, respectively; a plurality of axially spaced serrations 138 disposed along outer surface 431, 471, 481, 491, respectively; and a bevel 140 disposed along outer surface 431, 471, 481, 491 at end 430*b*, 470*b*, 480*b*, 490*b*, respectively. Serrations 138 are disposed along the inside of each leg 430, 470, 480, 490 (relative to central axis 405), and bevel 140 is disposed on the outside of each leg 430, 470, 480, 490 (relative to central axis 405). Serrations 138 and bevel 140 are as previously described with respect to implant 100. The geometry of outer surfaces 431, 471, 481, 491 of legs 430, 470, 480, 490 may be different to accommodate the particular surgical implementation. In the embodiment shown in FIG. 8, outer surface 431, 471, 481, 491 of each leg 430, 470, 480, 490 includes a cylindrical portion and a planar portion such that each leg 430, 470, 480, 490 has a D-shaped cross-section (e.g., similar to profile 260 of section 6 in FIGS. 4 and 6).

Referring still to FIG. 8, as previously described, central axis 415 of bridge 410 is curved. Similar to central axis 115 of bridge 110 previously described, the central axis 415 may have a constant or variable radius of curvature $R_{415}$ measured in the reference plane in front view (FIG. 8) from a point along central axis 405 to central axis 415 of bridge 310. In this embodiment, the radius of curvature $R_{415}$ of central axis 415 of bridge 410 varies continuously along its length between ends 410*a*, 410*b*. In particular, the radius of curvature $R_{415}$ of central axis 415 of bridge 410 is greatest at end 410*a* and gradually decreases moving toward end 410*b*. Such a variable radius of curvature may be advantageous to tailor the shape of bridge 410 to match a particular anatomical surgical site. Therefore, in other embodiments, the radius of curvature $R_{415}$ of central axis 415 of bridge 410 may increase, decrease, or sequentially increase and decrease between ends 410*a*, 410*b* of bridge 410.

Similar to implant 100, implant 400 includes smooth concave transitions 444 that blend ends 430*a*, 470*a*, 480*a*, 490*a* of legs 430, 470, 480, 490, respectively, and lower surface 114 of bridge 410. Adjacent transition surfaces 444 and proximal ends 430*a*, 490*a* of outer legs 430, 490, the portions of bridge 410 at ends 410*a*, 410*b* that extend laterally (relative to the reference plane) beyond legs 430, 490 along lower surface 114 include a pair of laterally opposed, downward facing planar shoulders 442 and a pair of laterally opposed, downward facing concave cavities or recesses 446. In addition, adjacent transition surfaces 444 and proximal ends 470*a*, 480*a* of inner legs 470, 480, the portions of bridge 410 that extends laterally (relative to the reference plane) beyond legs 470, 480 include a pair of laterally opposed, downward facing concave cavities or recesses 446. In this embodiment, shoulders 442 are oriented perpendicular to the reference plane and recesses 446 have semi-cylindrical geometries. Shoulders 442 and/or recesses 446 are sized and positioned to mate and engage with a device for manipulating, inserting, or positioning implant 400. Accordingly, shoulders 442 and recesses 446 may also be described as tool engagement shoulders 442 and tool engagement recesses 446, respectively.

At each end 410*a*, 410*b* of bridge 410, the pair of shoulders 442 and the pair of recesses 446 are disposed on opposite sides of axis 415 and the reference plane; and proximal transition surfaces 444 of inner legs 470, 480, the pair of recesses 446 are disposed on opposite sides of axis 415 and the reference plane. Thus, it should be appreciated that although only two shoulders 442 and four recesses 446 are shown in the front view of FIG. 8, four shoulders 442 and eight recesses 446 are included as implant 400 is symmetric about the reference plane, and thus, two additional shoulders 442 and four additional recesses 446 are included along the opposite side of implant 400. Shoulders 442 and recesses 446 may be useful in reducing bending stress concentrations and may be used to grip implant 400 with a surgical insertion or retaining tool. In particular, forces may be applied to implant 400 at shoulders 442 and/or recesses 446 to restrain or impart bending moments into bridge 410.

Figure 9:
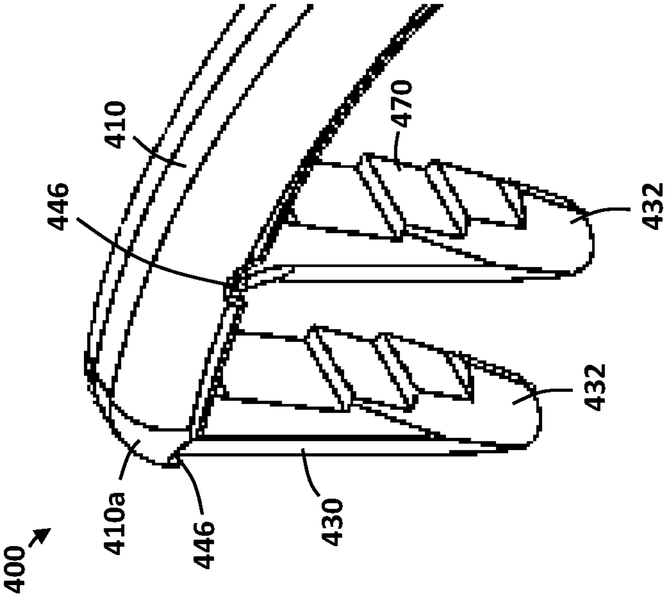
FIG. 9 is an enlarged, partial isometric view of the implant of FIG. 8.

Referring to FIGS. 8 and 9, in this embodiment, each leg 430, 470, 480, 490 also includes a conical tip 432 at second end 430*b*, 470*b*, 480*b*, 490*b*, respectively, which may be used to guide implant 400 as it is inserted into a drilled hole (e.g., as shown in FIG. 1 at holes 14, 16).

In this embodiment, implant 400 is made of a Nitinol material, and thus, can be heat treated and programed, as discussed above, to have shape memory and superelastic/pseudoelastic characteristics such that implant 400 may be classified as a superelastic shape memory implant, and may transform from one shape to another when exposed to heat.

Figure 10:
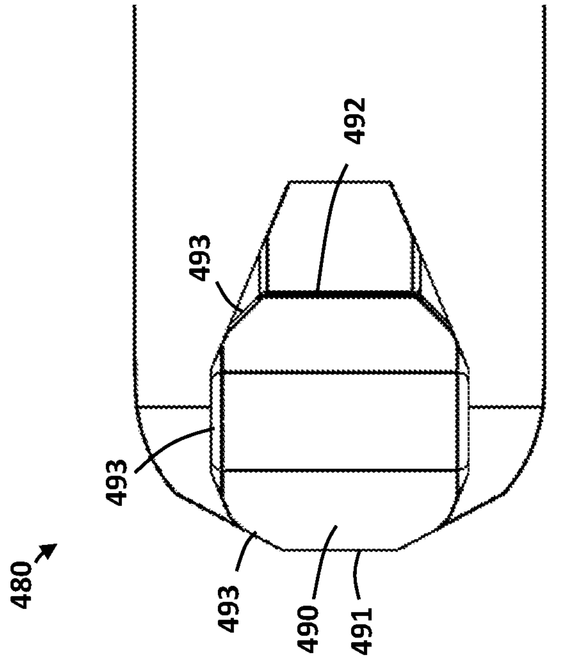
FIG. 10 is an enlarged, partial bottom view of an embodiment of an implant for compressing two bone segments together in accordance with the principles described herein.

Referring now to FIG. 10, a partial bottom view of an embodiment of a staple-style implant 480 is shown. In general, implant 480 can be used in place of implant 100 previously described and shown in FIG. 1. The legs of each implant 100, 200, 300, 400, 480 previously described may include any cross-sectional shape. As shown in FIG. 10, implant 480 includes a leg 490 having polygonal cross-sectional shape including an outer flat 491, an inner flat 492, and a plurality of chamfers or facets 493 extending therebetween.

To further illustrate various illustrative embodiments of the present disclosed technology, the following table provides exemplary force and section modulus comparisons between round cross-section and rectangular cross-section legs, when installed within a given drilled hole diameter.

TABLE 1

Force and section modulus comparison of rectangular vs cylindrical legs

| Cross-section | Drill Diameter, mm | b, mm | h, mm | c, mm | I, $mm^4$ | $S_{rectangular}$ = I/c |
|---|---|---|---|---|---|---|
| Rectangular | 2.0 | 1.0 | 1.5 | 0.75 | 0.28 | 0.38 |
| Rectangular | 2.5 | 1.3 | 2.0 | 1.00 | 0.89 | 0.89 |
| Rectangular | 3.0 | 1.7 | 2.5 | 1.25 | 2.18 | 1.74 |
| Rectangular | 3.5 | 2.0 | 3.0 | 1.50 | 4.52 | 3.02 |
| Rectangular | 4.0 | 2.3 | 3.5 | 1.75 | 8.38 | 4.79 |

TABLE 1-continued

Force and section modulus comparison of rectangular vs cylindrical legs

| | | d, mm | c, mm | I, $mm^4$ | $S_{cylinder} = I/c$ | $S_{cylinder}/S_{rectangular}$ Section Modulus Ratio | $F_{cylinder}/F_{rectangular}$ Force Ratio |
|---|---|---|---|---|---|---|---|
| Cylinder | 2.0 | 2.0 | 1.00 | 0.79 | 0.79 | 2.1 | 2.1 |
| Cylinder | 2.5 | 2.5 | 1.25 | 1.92 | 1.53 | 1.7 | 1.7 |
| Cylinder | 3.0 | 3.0 | 1.50 | 3.98 | 2.65 | 1.5 | 1.5 |
| Cylinder | 3.5 | 3.5 | 1.75 | 7.37 | 4.21 | 1.4 | 1.4 |
| Cylinder | 4.0 | 4.0 | 2.00 | 12.57 | 6.28 | 1.3 | 1.3 |

Ir = the modulus of rectangular cross-section.
Ic = the modulus of cylindrical cross-section.
$F_{rectangular}$ = the force at tip of legs for rectangular cross-section.
$F_{cylinder}$ = the force at tip of legs for cylindrical cross-section.
S = section modulus Referring to Table 1, cylindrical legs having a round cross-section demonstrate an increased section modulus as compared to legs having a rectangular cross-section, and thus are able to impart or react greater forces with each leg. Greater leg stiffness and higher forces provided by each leg may thus provide enhanced fixation and stability at a fracture, osteotomy or arthrodesis site (e.g., compression 18 across break 12 as shown in FIG. 1) to enable fusion. As shown in Table 1 as "section modulus ratio" and "force ratio", some embodiments including cylindrical legs may provide between approximately 1.3 to approximately 2.1 greater forces and section modulus as compared to legs having a rectangular cross-section.

In general, embodiments of staple-style implants disclosed herein (e.g., implants 100, 200, 300, 400, 480) can be held, retained, manipulated, and installed in bone or other anatomical site using any suitable and compatible devices or instruments. Exemplary embodiments of devices that can be used to hold, retain, manipulate, or install embodiments of implants disclosed herein will now be described. Such exemplary embodiments will be shown and described in connection with implant 100 previously described, however, it should be appreciated that the exemplary embodiments can be used with other embodiments of staple-style implants such as implants 200, 300, 400.

Figure 12:
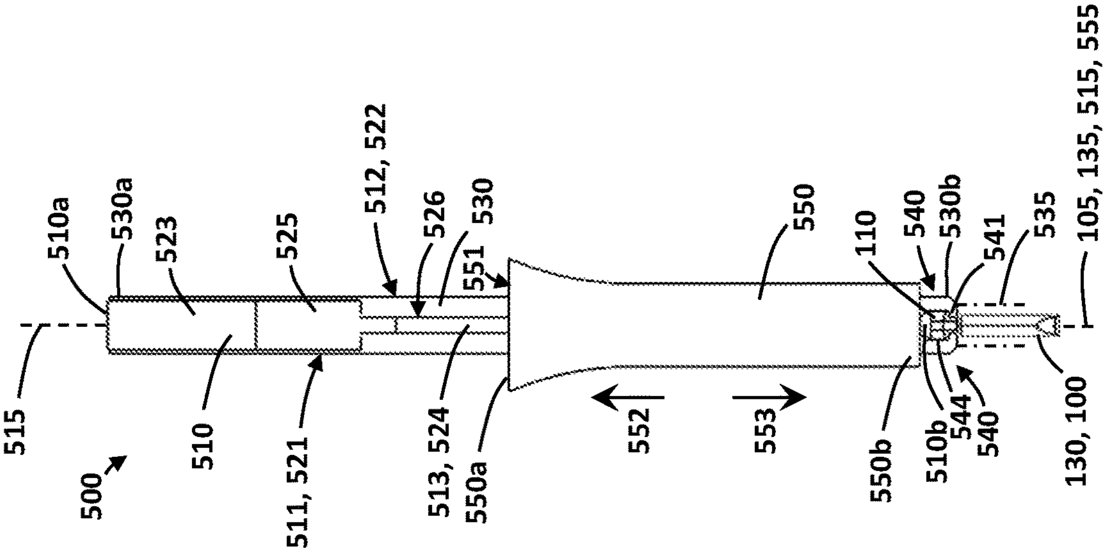
FIG. 12 is a side view of the insertion device of FIG. 11.
Figure 11:
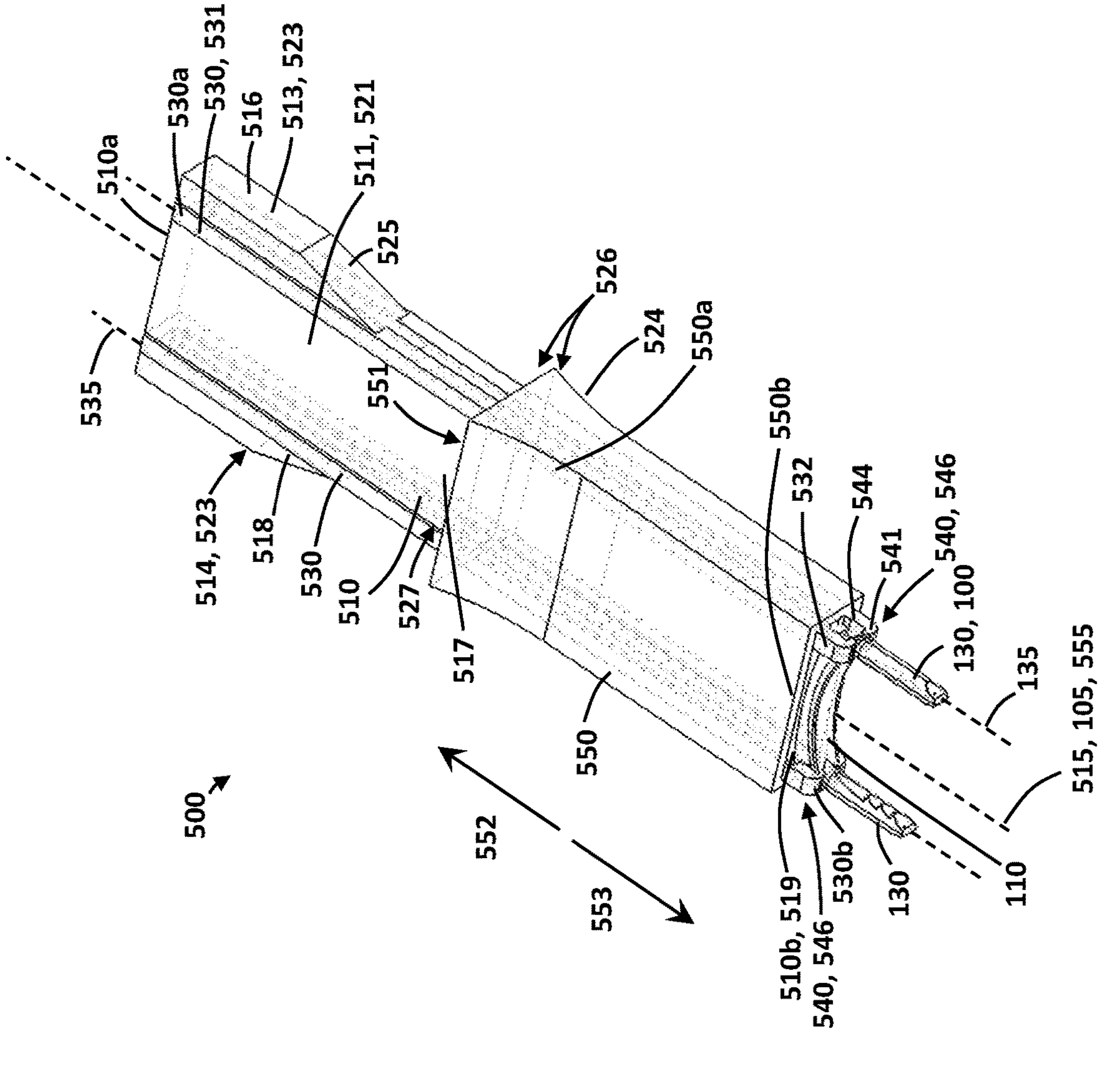
FIG. 11 is an isometric view of an embodiment of an insertion device for installing embodiments of implants disclosed herein in accordance with the principles described herein and with the jaws in the closed positions.
Figure 14:
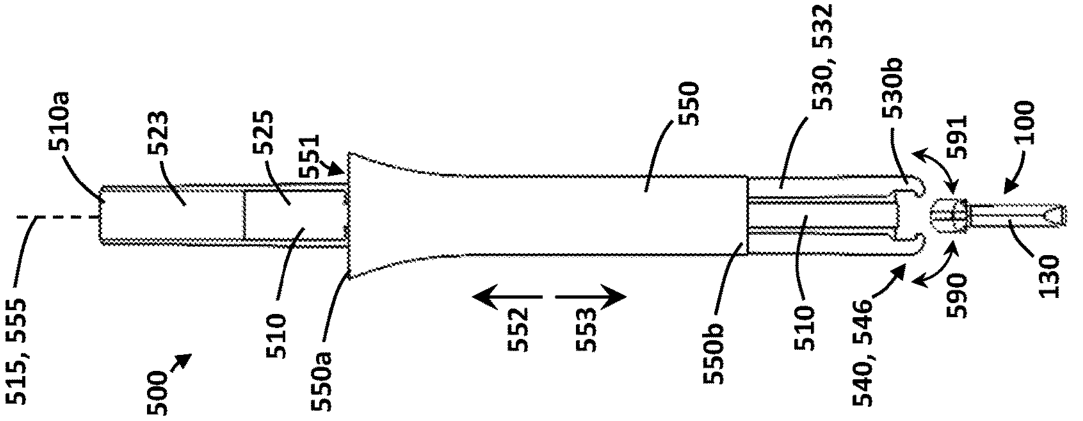
FIG. 14 is a side view of the implant insertion device of FIG. 13.
Figure 13:
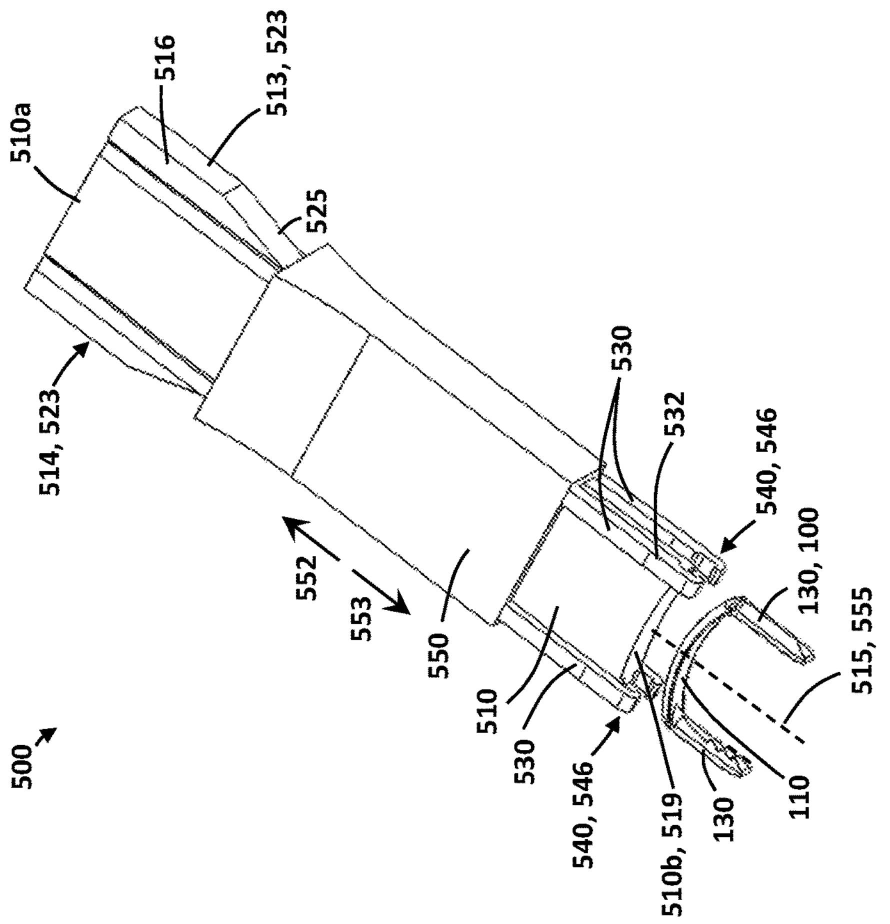
FIG. 13 is an isometric view of the implant insertion device of FIG. 11 with the jaws in the open positions.

Referring now to FIGS. 11-14, an embodiment of an insertion device 500 for holding, manipulating, and installing staple-style implant 100 is shown. As will be described in more detail below, device 500 can be operated by a surgeon or other user to securely hold implant 100 such as during installation in bone segments 2, 4, and selectively release implant 100 after installation in bone segments 2, 4. Thus, insertion device 500 may be described has having a first or closed configuration for securely gripping and holding implant 100 (e.g., for and during installation), and a second or open configuration for disengaging and releasing implant 100 (e.g. following installation). In FIGS. 11 and 12, insertion device 500 is shown in the first configuration securely holding implant 100, and in FIGS. 13 and 14, insertion device 500 is shown in the second configuration decoupled from implant 100.

In this embodiment, insertion device 500 includes a base 510, a plurality of resilient arms 530 flexibly and pivotally coupled to base 510, and a sleeve 550 slidably disposed about base 510 and arms 530. Base 510 is a rigid body having a central or longitudinal axis 515, a first end 510*a*, a second end 510*b* opposite end 510*a*, a front side 511 extending axially from end 510*a* to end 510*b*, a rear side 512 extending axially from end 510*a* to end 510*b*, and a pair of lateral sides 513, 514 extending axially from end 510*a* to end 510*b*. Each lateral side 513, 514 extends between sides 511, 512, and each side 511, 512 extend laterally between sides 513, 512.

In this embodiment, front side 511 comprises a planar face or surface 521 extending axially between ends 510*a*, 510*b* and rear side 512 comprises a planar face or surface 522 extending axially between ends 510*a*, 510*b*. Surfaces 521, 522 are oriented parallel to each other and axis 515. In addition, in this embodiment, each lateral side 513, 514 includes a planar surface 523 extending axially from end 510*a*, a planar surface 524 extending axially from end 510*b*, and a planar surface 525 extending between surfaces 523, 524. Surfaces 523, 524 are oriented parallel to axis 515 and oriented perpendicular to surfaces 521, 522. In addition, surfaces 523 are laterally opposite each other across axis 515, and surfaces 524 are laterally opposite each other across axis 515. Surfaces 525 are also oriented perpendicular to surfaces 521, 522, but are oriented at acute angles relative to axis 515. In particular, surfaces 525 taper inward toward axis 515 and slope toward each other moving axially from surface 523 to surface 524. Further, surfaces 525 are laterally opposite each other across axis 515. In this embodiment, each side 511, 512 includes a pair of elongate recesses 526, 527 in planar surface 521, 522, respectively. Recesses 526 extend axially from end 510*a* to end 510*b* along surfaces 521, 522 and are positioned adjacent lateral side 513, and recesses 527 extend axially from end 510*a* to end 510*b* along surfaces 521, 522 and are positioned adjacent lateral side 514.

Base 510 has a length measured axially from end 510*a* to end 510*b*, a width measured laterally and perpendicular to axis 515 from side 513 to side 514, and a thickness measured perpendicular to axis 515 (and surfaces 521, 522) from front side 511 to rear side 512. Front surface 521 and rear surface 522 are oriented parallel to each other, and thus, the thickness of base 510 is uniform and constant moving axially between ends 510*a*, 510*b*. Surfaces 523 are oriented parallel to each other and laterally opposed, and thus, the width of base is uniform and constant moving axially along surfaces 523 from end 510*a*; surfaces 524 are oriented parallel to each other and laterally opposed, and thus, the width of base is uniform and constant moving axially along surfaces 524 from end 510*b*; and surfaces 525 taper inward moving from surfaces 523 to surfaces 524, and thus, the width decreases moving axially along surfaces 525 from surfaces 524 to surfaces 525. Therefore, the width of base 510 is greatest along surfaces 523 extending from end 510*a*, and least along surfaces 524. Accordingly, body 510 may be described as having a first or wide section 516 extending from end 510*a*, a second or narrow section 517 extending from end 510*b*, and a transition section 518 extending between sections 516, 517. As will be described in more detail below, during use, insertion device 500 is physically held by the user along wide section 516, while sleeve 550 can be slid axially along narrow section 517 between end 510*b* and transition section 518. Consequently, wide section 516 may also be referred to herein as a handle.

Referring still to FIGS. 11-14, arms 530 are flexibly coupled to base 510. In particular, each arm 530 is an elongate resilient structure having a central or longitudinal axis 535, a first end 530*a* coupled to base 510, and a second or free end 530*b* distal base 510. Each arm 530 is at least partially seated in one of the recesses 526, 527. In particular, a portion of each arm 530 is disposed in a corresponding recess 526, 527 and a portion of each arm 530 extends axially from the corresponding recess 526, 527 at end 510*b* of base 510. Arms 530 and recesses 526, 527 are sized and shaped to mate with each other such that the portions of arms 530 disposed in recesses 526, 527 of front side 511 do not extend beyond surface 521 or extend beyond surfaces 524 when fully seated in recesses 526, 527 of front side 511, and such that the portions of arms 530 disposed in recesses 526, 527 of rear side 512 do not extend beyond surface 522 or extend beyond surfaces 524 when fully seated in recesses 526, 527 of rear side 512.

Each end 530*b* includes a claw 540 for releasably engaging implant 100, and in particular, for releasably engaging bridge 110 of implant 100. Each claw 540 has a shape and geometry to conform and mate with an end 110*a*, 110*b* of bridge 110. More specifically, each claw 540 is generally C-shaped in side view (FIGS. 12 and 14) including a tip 541 and a pocket 544 axially adjacent tip 541. Each tip 541 is sized and shaped to mate and engage a corresponding recess 146 and shoulder 142 of bridge 110, and each pocket 544 sized to receive a corresponding lateral side of bridge 110 adjacent and above the recess 146. As will be described in more detail below, insertion device 500 is used to manipulate and install staple-style implant 100 in bone segments 2, 4. Each tip 541 is sized such that it does not interfere with axial advancement of legs 130 (relative to axes 130, 105) into holes 14, 16 or the placement of lower surface 114 of implant immediately adjacent or in direct contact with bone segments 2, 4 when implant 100 is installed in bone segments 2, 4 and tips 541 are seated in recesses 146 and engaging shoulders 142.

Referring still to FIGS. 11-14, each claw 540 faces and is opposed one other claw 540 to receive one end 110*a*, 110*b* of bridge 110 therebetween. Each pair of opposed claws 540 define a jaw 546 that releasably engages one end 110*a*, 110*b* of bridge 110 with tips 541 seated in the corresponding recesses 146 and engaging the corresponding shoulders 142. As will be described in more detail below, each jaw 546 has a closed position with the corresponding tips 541 seated in the corresponding recesses 146 and engaging the corresponding shoulder 142 when the corresponding end 110*a*, 110*b* of bridge 110 is disposed between the tips 541, and an open position with the corresponding tips 541 withdrawn and spaced from the corresponding recesses 146 and shoulders 142 when the corresponding end 110*a*, 110*b* of bridge 110 is disposed between the tips 541. When jaws 546 are in the open positions, bridge 110 is released by jaws 546 and is free to pass between tips 541 so as to allow decoupling and physical separation of insertion device 500 and implant 100. It is to be understood that insertion device 500 is in the first configuration for securely gripping and holding implant 100 when jaws 546 are in the closed positions shown in FIGS. 11 and 12, and insertion device 500 is in the second configuration for disengaging and releasing implant 100 when jaws 546 are in the open positions shown in FIGS. 13 and 14.

As previously described, legs 130 of implant 100 are inwardly biased and/or manufactured such that leg angles α increase and ends 130*b* move toward each other upon the application of heat. Arms 530 are sized and claws 540 are axially positioned relative to base 510 such that upper surface 112 of bridge 110 contacts end 510*b* of base 510 and ends 110*a*, 110*b* of bridge 110 are held in position by claws 540 with central axes 135 of legs 130 oriented parallel to central axes 105, 515 (i.e., leg angles α are 0°) when jaws 546 are in the closed positions and tips 541 are fully seated in mating recesses 146 and engaging the corresponding shoulders 142. As shown in FIG. 11, in embodiments described herein, end 510*b* of base 510 comprises a concave surface 519 extending between lateral sides 513, 514. Concave surface 519 has an apex or peak at central axis 515, thereby facilitating the lateral centering of implant 100 relative to end 510*b* (between arms 530) as convex upper surface 112 of bridge 110 engages end 510*b*.

As noted above, arms 530 are flexibly and pivotally coupled to base 510. In particular, each arm 530 includes a first section 531 that extends axially from end 510*a* and is fixably secured to base 510 such it cannot move translationally or rotationally relative to base 510, and a second section 532 that extends axially from first section 531 to end 510*b* and is free to resiliently pivot about the intersection of the second section 532 and the corresponding first section 531. First sections 531 are fully seated in the corresponding recess 526, 527, whereas second sections 532 can pivot in and out the corresponding recesses 526, 527 as jaws 546 transition between the closed and open positions, respectively. In this embodiment, second sections 532 are biased to pivot outwardly from the corresponding recesses 526, 527 and away from base 510 (generally in planes oriented parallel to axis 515 and perpendicular to surfaces 521, 522), but can be urged and elastically flex to pivot inwardly into the corresponding recesses 526, 527 and toward from base 510 (generally in planes oriented parallel to axis 515 and perpendicular to surfaces 521, 522) as schematically illustrated by arrows 590, 591 in FIG. 14. For example, arms 530 may be made of a generally rigid metal (e.g., stainless steel) that is linear along first section 531 between end 530*a* and second section 532 and linear along section 532 between end 530*b* and first section 531, but bent at the intersection of sections 531, 532 such that in the relaxed state second section 532 is oriented at an angle relative to first section 531. However, when an external force is applied to second section 532 with first section 531 held stationary, second section 532 can be elastically flexed into linear alignment with first section; and when the external force is subsequently remove, second section 532 resiliently rebounds from the flexed position to the relaxed position. In general, jaws 546 transition to the open positions when section sections 532 and associated ends 530*b* pivot outwardly away from base 510 (generally perpendicular to front and rear surfaces 521, 522), and jaws 546 transition to the closed positions when sections 532 and associated ends 530*b* pivot inwardly toward base 510 (generally perpendicular to front and rear surfaces 521, 522).

In this embodiment, the axial movement of sleeve 550 relative to base 510 and arms 530 selectively controls the transition of jaws 546 between the open and closed positions. In particular, sleeve 550 is slidably mounted to base 510 and disposed about base 510 and arms 530. Sleeve 550 has a central or longitudinal axis 555 coaxially aligned with axis 515, a first end 550*a*, a second end 550*b* opposite end 550*a*, and a through bore or passage 551 extending axially from end 550*a* to end 550*b*. The radially inner surface of sleeve 550 that defines passage 551 has a rectangular cross-sectional shape sized to conform with and slidingly engage narrow section 517. In other words, passage 551 is sized and shaped so that sleeve 550 slidingly engages planar surfaces 521, 522 of front and rear sides 511, 512, respectively, and planar surfaces 524 of lateral sides 513. Sleeve 550 has a length measured axially (relative to axes 515, 555) between ends 550*a*, 550*b* that is less than a length of narrow section 517 measured axially (relative to axes 515, 555) between end 550*a* and transition section 518. Thus, sleeve 550 can be moved axially (relative to axes 515, 555) along narrow section 517 away from end 510*b* and toward end

510*a* in a first axial direction 552, and moved axially (relative to axes 515, 555) along narrow section 517 away from end 510*a* and toward end 510*b* in a second axial direction 553 that is opposite first axial direction 552. As previously described, second sections 532 are biased outwardly, and thus, as sleeve 550 moves axially away from end 510*b* in first axial direction 552, second sections 532 are permitted to resiliently pivot outwardly, thereby allowing jaws 546 to transition to the open positions; and as sleeve 550 moves axially toward end 510*b* in second axial direction 553, sleeve 550 bears against second sections 532 and urges second sections 532 into recesses 526, 527, thereby transitioning jaws 546 to the closed position. As the axial movement of sleeve 550 in axial directions 531, 532 transitions jaws 546 between the closed and open positions, respectively, sleeve 550 may also be referred to herein as an actuator.

As previously described, insertion device 500 can releasably hold implant 100, and be used to position and install implant 100 in bone segments 2, 4 to enable to application of compression 18 across break 12. The installation of implant using insertion device 500 will now be described. Referring first to FIGS. 11 and 12, insertion device 500 is in the first configuration with jaws 546 in the closed positions securely holding and gripping implant 100 with mating tips 541. As previously described, with jaws 546 in the closed positions, upper surface 112 of bridge 110 bears against end 510*b* of base 510 and ends 110*a*, 110*b* of bridge 110 are held in position by jaws 546 with legs 130 oriented parallel to central axes 105, 515. Thus, in FIGS. 11 and 12, legs 130 are oriented parallel to central axes 105, 515. As best shown in FIG. 1, holes 14, 16 are drilled parallel to each other in bone segments 2, 4, respectively, and positioned and spaced to receive legs 130. While maintaining insertion device 500 in the first configuration with jaws 546 in the closed positions, insertion device 500 is used to position each end 130*a*, 130*b* adjacent a corresponding hole 14, 16 with each leg 130 coaxially aligned with a corresponding hole 14, 16. Next, insertion device 500 is used to insert legs 130 into holes 14, 16 and advance legs 130 through holes 14, 16. Due to engagement of outer surfaces 131 of legs 130 with bone segments 2, 4 and the interference fit therebetween, the user may use a mallet or other device to tap end 510*a* of base 510 and drive legs 130 into holes 14, 16 until legs 130 are sufficiently set in holes 14, 16 and bridge 110, and more specifically lower surface 114 of bridge 110, engages or is in immediately adjacent bone segments 2, 4. With implant 100 sufficiently seated in holes 14, 16, the user of insertion device 500 transitions insertion device 500 to the second configuration with jaws 546 in the open positions by sliding sleeve 550 axially along narrow portion away from end 510*b* and toward end 510*a*. As jaws 546 transition from the closed positions to the open positions, bridge 110 of implant is released by jaws 546. Once released, insertion device 500 is no longer applying forces to bridge 110 to maintain legs 130 in parallel orientations. Consequently, inwardly biased legs 130 generate and apply compressive loads 18 to break 12 and/or heat may be applied to implant 100 (body heat or external heat) to phase change implant 100 to enable legs 130 to apply or increase the application of compressive loads 18 to break 12.

Figure 15:
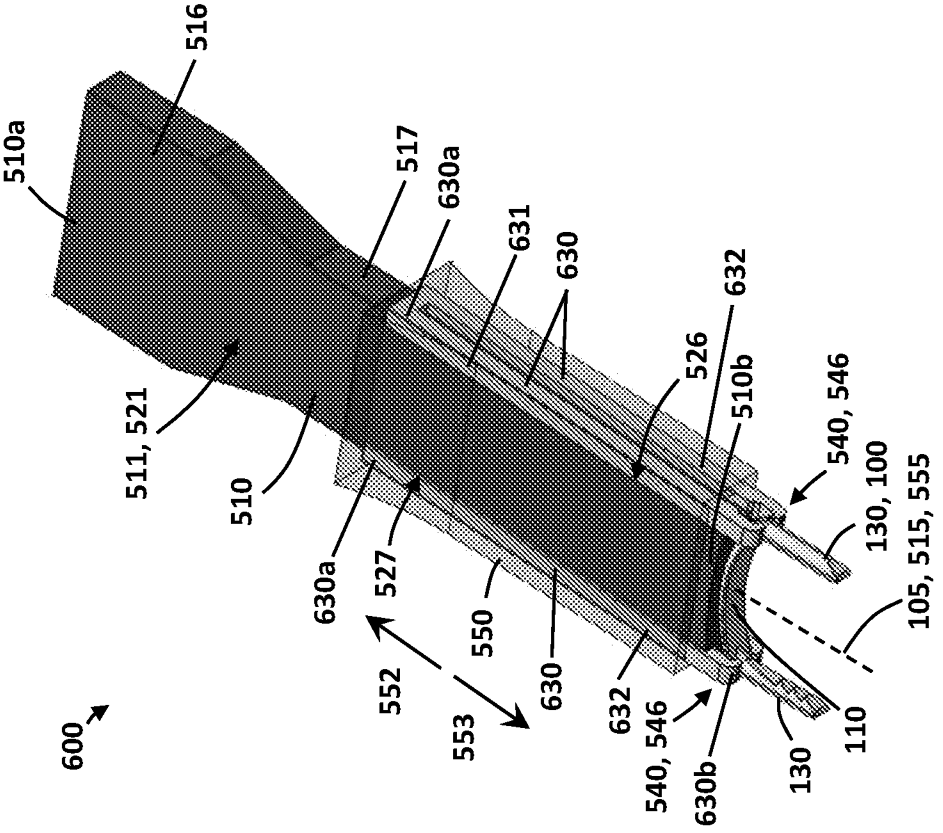
FIG. 15 is an isometric view of an embodiment of an insertion for installing embodiments of implants disclosed herein in accordance with the principles described herein and with the jaws in the closed positions.
Figure 16:
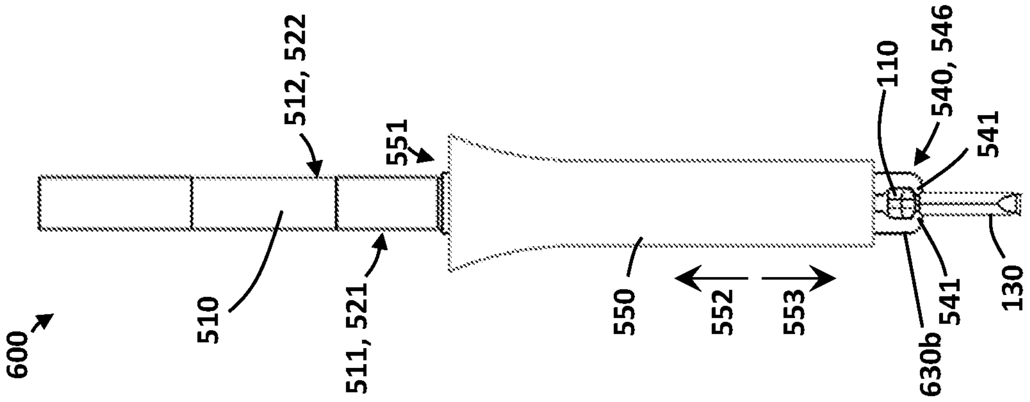
FIG. 16 is a side view of the implant insertion device of FIG. 15.
Figure 18:
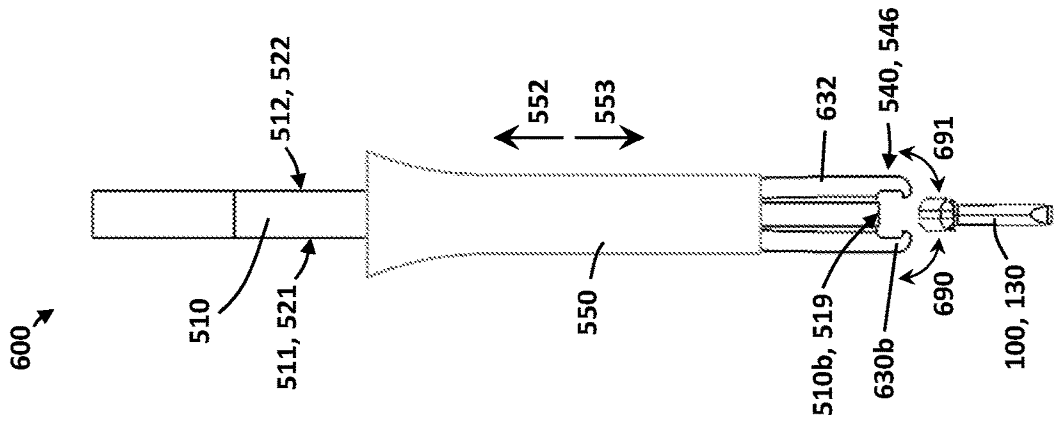
FIG. 18 is a side view of the implant insertion device of FIG. 17.

Referring now to FIGS. 15-18, an embodiment of an insertion device 600 for holding, manipulating, and installing staple-style implant 100 is shown. Device 600 is operated in the same manner as device 500 previously described, and thus, device 600 can be operated by a surgeon or other user to securely hold implant 100 such as during installation in bone segments 2, 4, and selectively release implant 100 after installation in bone segments 2, 4. Thus, insertion device 600 may also be described has having a first or closed configuration for securely gripping and holding implant 100 (e.g., for and during installation), and a second or open configuration for disengaging and releasing implant 100 (e.g. following installation). In FIGS. 15 and 16, insertion device 600 is shown in the first configuration securely holding implant 100, and in FIGS. 17 and 18, insertion device 600 is shown in the second configuration decoupled from implant 100.

Figure 17:
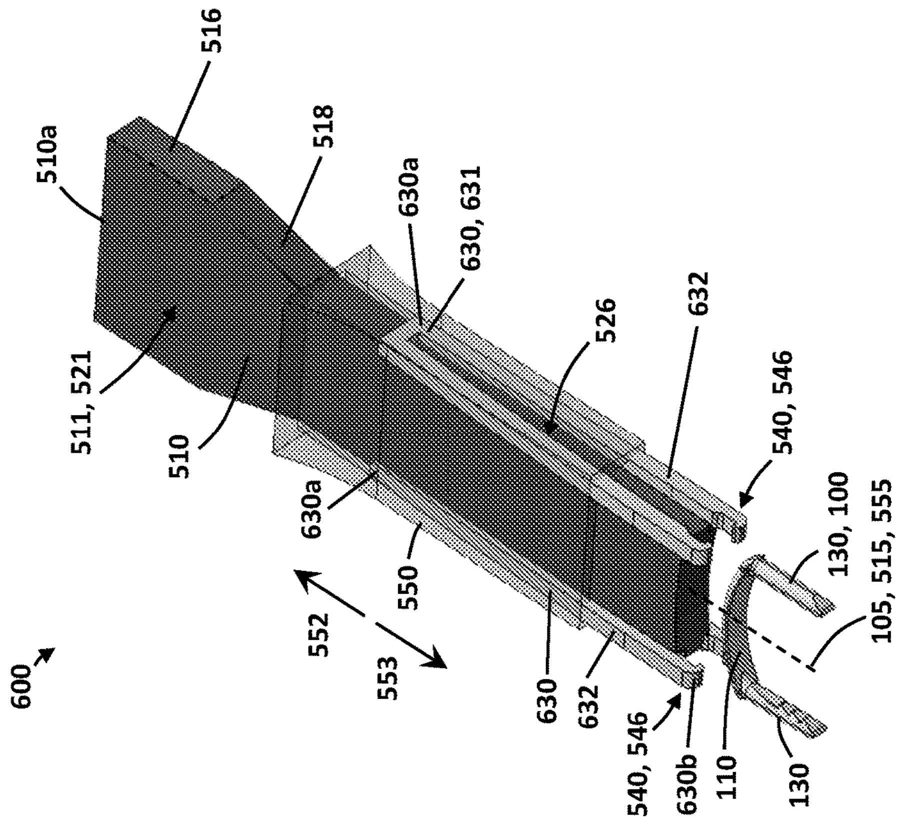
FIG. 17 is an isometric view of the implant insertion device of FIG. 15 with the jaws in the open positions.

Insertion device 600 is substantially the same as insertion device 500 previously described. In particular, insertion device 600 includes a base 510, a plurality of resilient arms 630 flexibly and pivotally coupled to base 510, and a sleeve 550 slidably disposed about base 510 and arms 630. Base 510 and sleeve 550 are both as previously described with respect to insertion device 500. In FIGS. 15 and 17, sleeve 550 is shown in phantom so that the portions of arms 630 disposed within sleeve 550 can be seen.

Arms 630 are similar to arms 530. In particular, arms 630 are flexibly coupled to base 510. Each arm 630 is an elongate resilient structure having a central or longitudinal axis 635, a first end 630*a* coupled to base 510, and a second or free end 630*b* distal base 510. Each arm 630 is at least partially seated in one of the recesses 526, 527 in base 510. In particular, a portion of each arm 630 is disposed in a corresponding recess 526, 527 and a portion of each arm 630 extends axially from the corresponding recess 526, 527 at end 510*b* of base 510. Arms 630 and recesses 526, 527 are sized and shaped to mate with each other such that the portions of arms 630 disposed in recesses 526, 527 of front side 511 do not extend beyond surface 521, and such that the portions of arms 530 disposed in recesses 526, 527 of rear side 512 do not extend beyond surface 522. However, in this embodiment, each arm 630 extends laterally from narrow section 517 of base 510 beyond the corresponding surface 524 when fully seated in the corresponding recess 526, 527.

Ends 630*b* of arms 630 are the same as ends 530*b* of arms 530 previously described. Namely, each end 630*b* includes a claw 540 as previously described. In addition, each claw 540 faces and is opposed one other claw 540 to receive one end 110*a*, 110*b* of bridge 110 therebetween. Each pair of opposed claws 540 define a jaw 546 as previously described for releasably engaging one end 110*a*, 110*b* of bridge 110 with tips 541 seated in the corresponding recesses 146 and engaging the corresponding shoulders 142. However, unlike arms 530 previously described, in this embodiment, upper ends 630*a* of arms 630 are coupled along narrow section 517, and thus, arms 630 do not extend axially into transition section 518 or wide section 516 of base 510.

Similar to arms 530 previously described, arms 630 are flexibly and pivotally coupled to base 510. In particular, each arm 630 includes a first section 631 that extends axially from end 630*a* and is fixably secured to base 510 such it cannot move translationally or rotationally relative to base 510, and a second section 632 that extends axially from first section 631 to end 630*b* and is free to resiliently pivot about the intersection of the second section 632 and the corresponding first section 631. First sections 631 are fully seated in the corresponding recess 526, 527, whereas second sections 632 can pivot in and out the corresponding recesses 526, 527 as jaws 546 transition between the closed and open positions, respectively. In this embodiment, second sections 632 are biased to pivot outwardly from the corresponding recesses 526, 527 and away from base 510 (generally in planes oriented parallel to axis 515 and perpendicular to surfaces 521, 522), but can be urged and elastically flex to pivot inwardly into the corresponding recesses 526, 527 and toward from base 510 (generally in planes oriented parallel to axis 515 and perpendicular to surfaces 521, 522) as schematically illustrated by arrows 690, 691 in FIG. 18. For example, arms 630 may be made of a generally rigid metal (e.g., stainless steel) that is linear along first section 631 between end 630*a* and second section 632 and linear along section 632 between end 630*b* and first section 631, but bent at the intersection of sections 631, 632 such that in the relaxed state second section 632 is oriented at an angle relative to first section 631. However, when an external force is applied to second section 632 with first section 631 held stationary, second section 632 can be elastically flexed into linear alignment with first section; and when the external force is subsequently remove, second section 632 resiliently rebounds from the flexed position to the relaxed position. In general, jaws 546 transition to the open positions when section sections 632 and associated ends 630*b* pivot outwardly away from base 510 (generally perpendicular to front and rear surfaces 521, 522), and jaws 546 transition to the closed positions when sections 632 and associated ends 630*b* pivot inwardly toward base 510 (generally perpendicular to front and rear surfaces 521, 522). In the same manner as previously described with respect to insertion device 500, in this embodiment, the axial movement of sleeve 550 relative to base 510 and arms 630 selectively controls the transition of jaws 546 between the open and closed positions.

Arms 630 are sized and claws 540 are axially positioned relative to base 510 such that upper surface 112 of bridge 110 contacts end 510*b* of base 510 and ends 110*a*, 110*b* of bridge 110 are held in position by claws 540 with central axes 135 of legs 130 oriented parallel to central axes 105, 515 (i.e., leg angles $\alpha$ are 0°) when jaws 546 are in the closed positions, tips 541 are fully seated in mating recesses 146, and tips 541 engage shoulders 142. Insertion device 600 is operated in the same manner as insertion device 500 previously described to releasably hold implant 100, position implant 100, and install implant 100 in bone segments 2, 4 to enable to application of compression 18 across break 12.

Figure 19:
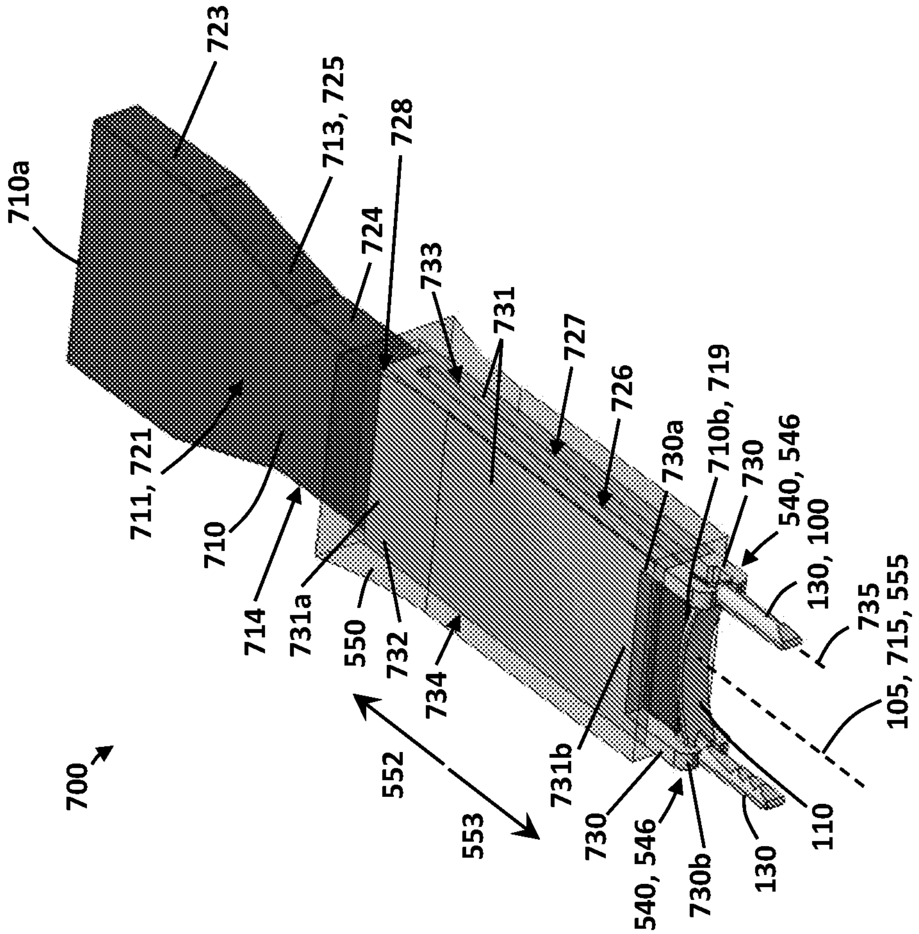
FIG. 19 is an isometric view of an embodiment of an insertion for installing embodiments of implants disclosed herein in accordance with the principles described herein and with the jaws in the closed positions.
Figure 20:
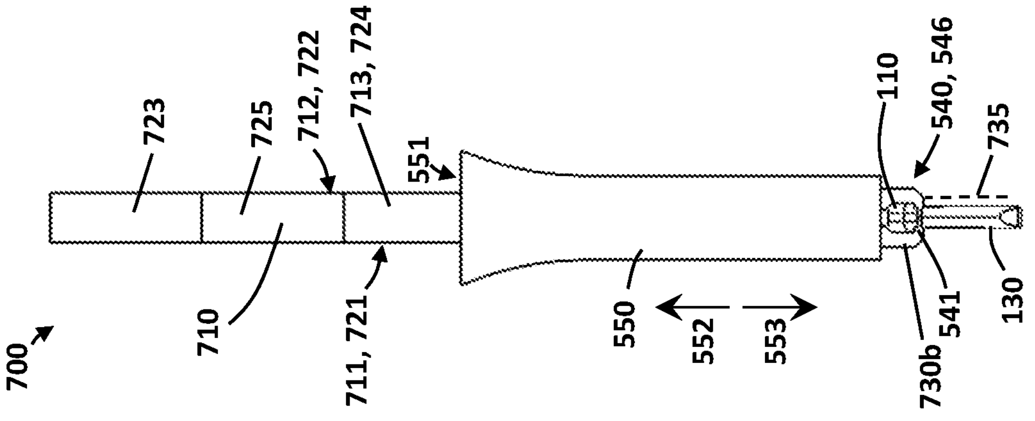
FIG. 20 is a side view of the implant insertion device of FIG. 19.
Figure 22:
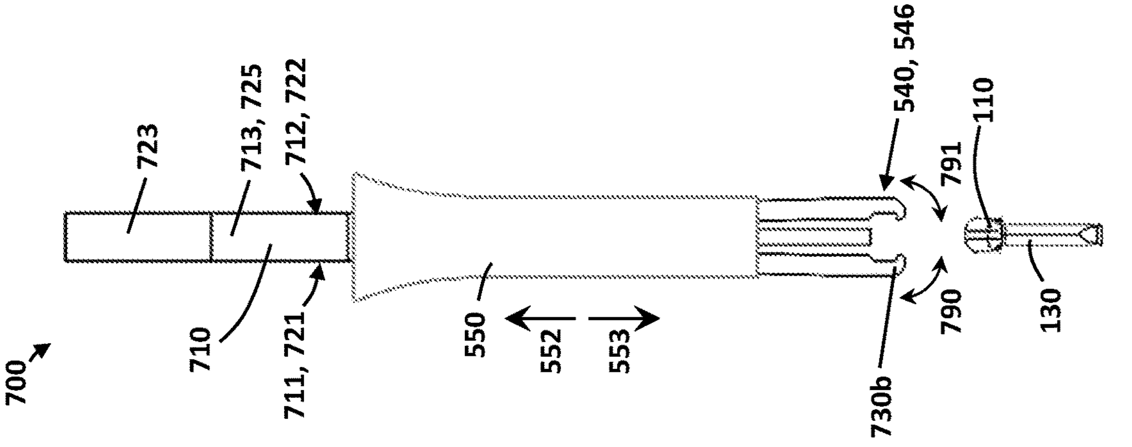
FIG. 22 is a side view of the implant insertion device of FIG. 21.
Figure 21:
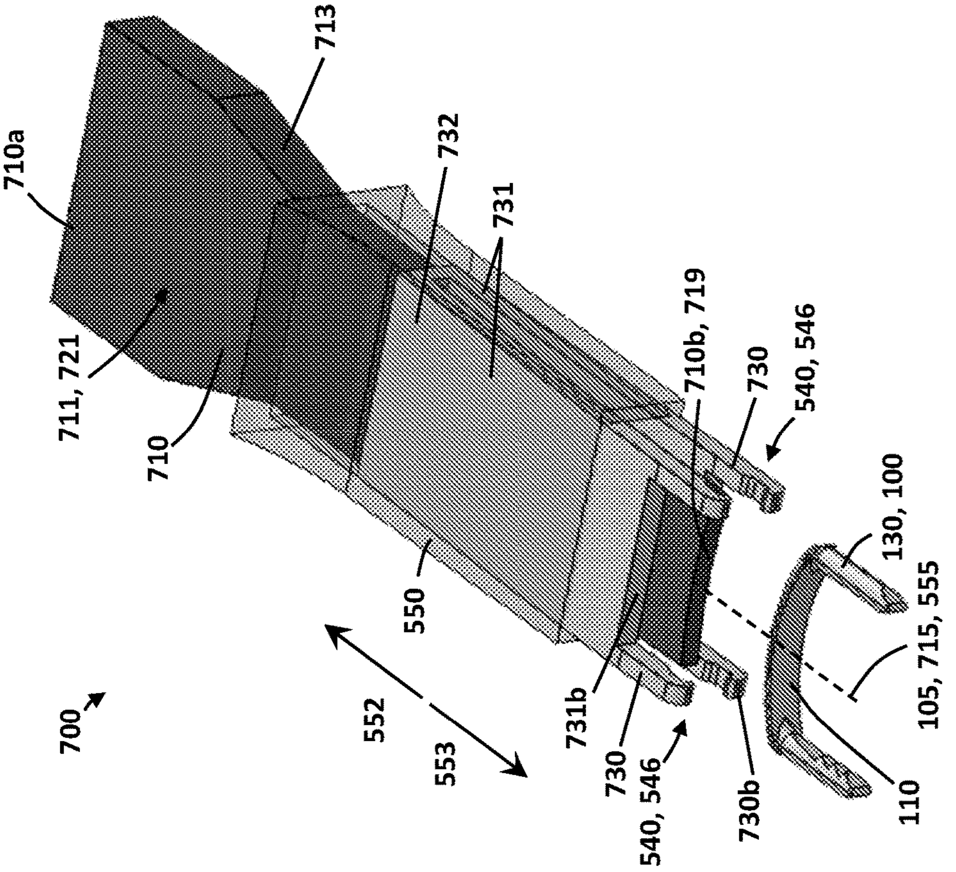
FIG. 21 is an isometric view of the implant insertion device of FIG. 19 with the jaws in the open positions.

Referring now to FIGS. 19-22, an embodiment of an insertion device 700 for holding, manipulating, and installing staple-style implant 100 is shown. Device 700 is operated in the same manner as device 500 previously described, and thus, device 700 can be operated by a surgeon or other user to securely hold implant 100 such as during installation in bone segments 2, 4, and selectively release implant 100 after installation in bone segments 2, 4. Thus, insertion device 700 may also be described has having a first or closed configuration for securely gripping and holding implant 100 (e.g., for and during installation), and a second or open configuration for disengaging and releasing implant 100 (e.g. following installation). In FIGS. 19 and 20, insertion device 700 is shown in the first configuration securely holding implant 100, and in FIGS. 21 and 22, insertion device 700 is shown in the second configuration decoupled from implant 100. In FIGS. 19 and 21, sleeve 550 is shown in phantom so that structures within sleeve 550 can be seen.

Insertion device 700 is substantially the same as insertion devices 500, 600 previously described. In particular, insertion device 700 includes a base 710, a plurality of resilient arms 730 flexibly and pivotally coupled to base 710, and a sleeve 550 slidably disposed about base 710 and arms 730. Sleeve 550 is as previously described with respect to insertion device 500, and base 710 is substantially the same as base 510 previously described with the exception that recesses 526, 527 in surfaces 521, 522, respectively, are replaced with recesses 726, 727. More specifically, base 710 is a rigid body having a central or longitudinal axis 715, a first end 710*a*, a second end 710*b* opposite end 710*a*, a front side 711 extending axially from end 710*a* to end 710*b*, a rear side 712 extending axially from end 710*a* to end 710*b*, and a pair of lateral sides 713, 714 extending axially from end 710*a* to end 710*b*. Each lateral side 713, 714 extends between sides 711, 712, and each side 711, 712 extends laterally between sides 713, 712.

In this embodiment, front side 711 comprises a planar face or surface 721 extending axially from end 710*a* and rear side 712 comprises a planar face or surface 722 extending axially from end 710*a*. Surfaces 721, 722 are oriented parallel to each other and axis 715. However, in this embodiment, planar surfaces 721, 722 do not extend axially to end 710*b*, as base 710 includes recesses 726, 727 extending axially along sides front and rear sides 711, 712, respectively, from end 710*b* to a shoulder 728 disposed between ends 710*a*, 710*b*. Recesses 726, 727 extend laterally completely across base 710 from lateral side 713 to lateral side 714.

Each lateral side 713, 714 includes a planar surface 723 extending axially from end 710*a*, a planar surface 724 extending axially from end 710*b*, and a planar surface 725 extending between surfaces 723, 724. Surfaces 723, 724 are oriented parallel to axis 715 and oriented perpendicular to surfaces 721, 722. In addition, surfaces 723 are laterally opposite each other across axis 715, and surfaces 724 are laterally opposite each other across axis 715. Surfaces 725 are also oriented perpendicular to surfaces 721, 722, but are oriented at acute angles relative to axis 715. In particular, surfaces 725 taper inward toward axis 715 and slope toward each other moving axially from surface 723 to surface 724. Further, surfaces 725 are laterally opposite each other across axis 715.

Referring still to FIGS. 19-22, arms 730 are similar to arms 630. In particular, arms 730 are flexibly coupled to base 710. However, in this embodiment, each arm 730 extends axially from a plate 731. More specifically, insertion device 700 includes two plates 731, with one plate 731 being seated in each recess 726, 727 along side 711, 712, respectively. Each plate 731 has first end 731*a*, a second end 731*b* opposite end 731*a*, and lateral sides 733, 734 extending laterally beyond surfaces 724 of base 710. Ends 731*b* are axially spaced from end 710*b* of base 710, and thus, plates 731 extend axially from shoulders 728 to locations between end 710*b* and shoulders 728. Plates 731 disposed along opposite sides 711, 712 are coupled together along lateral sides 733, 734 at first ends 731*a*. Sleeve 550 is disposed about base 710 and plates 731, and slidingly engages plates 731. In particular, passage 551 of sleeve 550 is sized and shaped to conform with plates 731, while allowing sleeve 550 to move axially relative to plates 731, arms 730, and base 710 in directions 552, 553.

In this embodiment, each arm 730 is integral with and extends axially from end 731*b* of one of the plates 731. In particular, each arm 730 is an elongate resilient structure having a central or longitudinal axis 735, a first end 730*a* fixably attached to and integral with a corresponding plate 731, and a second end 730*b* distal the corresponding plate 731 and extending axially beyond end 710*b* of base 710. Each arm 730 is at least partially seated in one of the recesses 726, 727 in base 710, and extends axially therefrom at end 710*b*. Ends 730*b* of arms 730 are the same as ends 530*b* of arms 530 previously described. Namely, each end 730*b* includes a claw 540 as previously described. In addition, each claw 540 faces and is opposed one other claw 540 to receive one end 110*a*, 110*b* of bridge 110 therebetween. Each pair of opposed claws 540 define a jaw 546 as previously described for releasably engaging one end 110*a*, 110*b* of bridge 110 with tips 541 seated in the corresponding recesses 146 and engaging corresponding shoulders 142.

Arms 730 are flexibly and pivotally coupled to base 710 via plates 731. In particular, each plate 731 includes a first section 732 extends axially from end 731*a* and is fixably secured to base 710 such it cannot move translationally or rotationally relative to base 710, and a second section 733 that extends axially from first section 732 to end 731*b* and is free to resiliently pivot about the intersection of the second section 733 and the corresponding first section 732. First sections 732 of plates 731 are fully seated in the corresponding recess 526, 527, whereas second sections 532 and arms 730 extending axially therefrom can pivot in and out the corresponding recesses 726, 727 as jaws 546 transition between the closed and open positions, respectively. In this embodiment, second sections 733 and arms 730 extending therefrom are biased to pivot outwardly from the corresponding recesses 726, 727 and away from base 710 (generally in planes oriented parallel to axis 715 and perpendicular to surfaces 721, 722), but can be urged and elastically flex to pivot inwardly into the corresponding recesses 726, 727 and toward from base 510 (generally in planes oriented parallel to axis 715 and perpendicular to surfaces 721, 722) as schematically illustrated by arrows 790, 791 in FIG. 22. For example, plates 731 may be made of a generally rigid metal (e.g., stainless steel) that is linear along first section 732 between end 731*a* and second section 733 and linear along second section 733 between end 731*b* and first section 732, but bent at the intersection of sections 732, 733 such that in the relaxed state second section 733 is oriented at an angle relative to first section 732. However, when an external force is applied to second section 733 with first section 732 held stationary, second section 733 can be elastically flexed into linear alignment with first section; and when the external force is subsequently remove, second section 733 resiliently rebounds from the flexed position to the relaxed position. In general, jaws 546 transition to the open positions when section sections 733 and associated ends 731*b* pivot outwardly away from base 510, and jaws 546 transition to the closed positions when sections 733 and associated ends 731*b* pivot inwardly toward base 510. In the same manner as previously described with respect to insertion device 500, in this embodiment, the axial movement of sleeve 550 relative to base 710, arms 730, and plates 731 selectively controls the transition of jaws 546 between the open and closed positions.

Arms 730 are sized and claws 540 are axially positioned relative to base 710 such that upper surface 112 of bridge 110 contacts end 710*b* of base 710 and ends 110*a*, 110*b* of bridge 110 are held in position by claws 540 with central axes 135 of legs 130 oriented parallel to central axes 105, 715 (i.e., leg angles $\alpha$ are 0°) when jaws 546 are in the closed positions and tips 541 are fully seated in mating recesses 146 and engage corresponding shoulders 142. Insertion device 700 is operated in the same manner as insertion device 500 previously described to releasably hold implant 100, position implant 100, and install implant 100 in bone segments 2, 4 to enable to application of compression 18 across break 12. Similar to base 510 previously described, in this embodiment, end 710*b* of base 710 comprises a concave surface 719 extending between lateral sides 713, 714. Concave surface 719 has an apex or peak at central axis 715, thereby facilitating the lateral centering of implant 100 relative to end 710*b* (between arms 730) as convex upper surface 112 of bridge 110 engages end 710*b*.

In the embodiments of insertion devices 500, 600, 700 described above, tips 541 and jaws 546 are sized and shaped to mate and engage with both a corresponding recess 146 and planar shoulder 142 of bridge 110. However, in other embodiments, the tips and jaws (e.g., tips 541 and jaws 546) at the ends of the legs (e.g., ends 530*b* of legs 530) that grasp the bridge (e.g., bridge 110) may be sized and shaped to mate and engage a planar shoulder (e.g., shoulder 142) at each end of the bridge but not a recess (e.g., recess 146) at each end of the bridge, or sized and shaped to mate and engage a corresponding recess (e.g., recess 146) at each end of the bridge but not a planar shoulder (e.g., shoulder 142) at each end of the bridge.

As previously described, insertion devices 500, 600, 700 can be used to hold, position, and install a staple-style implant such as implant 100 described herein with the legs of the implant (e.g., legs 130) maintained in a parallel orientation. Other devices that can also be used to hold and position embodiments of staple-style implants will now be described. Such exemplary embodiments will be shown and described in connection with implant 100 previously described, however, it should be appreciated that the exemplary embodiments can be used with other embodiments of staple-style implants such as implants 200, 300, 400.

Referring now to FIGS. 23-27, an embodiment of a retention device 800 for holding and positioning staple-style implant 100 is shown. As will be described in more detail below, device 800 can be operated by a surgeon or other user to securely hold implant 100.

Figure 24:
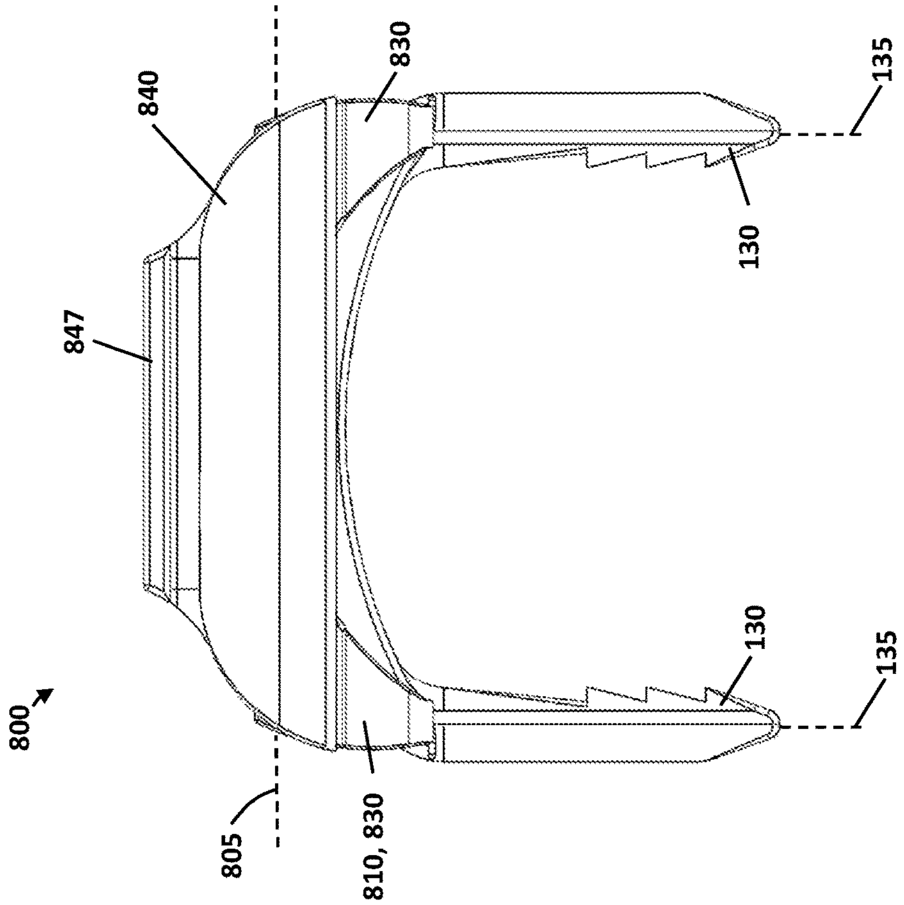
FIG. 24 is a front view of the retention device of FIG. 23.
Figure 23:
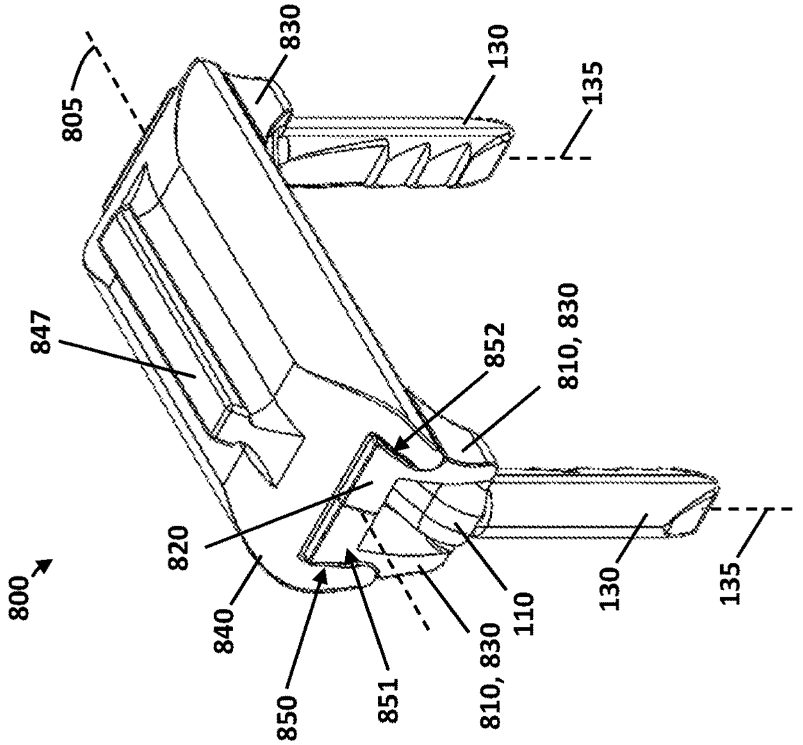
FIG. 23 is an isometric view of an embodiment of a retention device for holding and manipulating embodiments of implants disclosed herein in accordance with the principles described herein.
Figure 26:
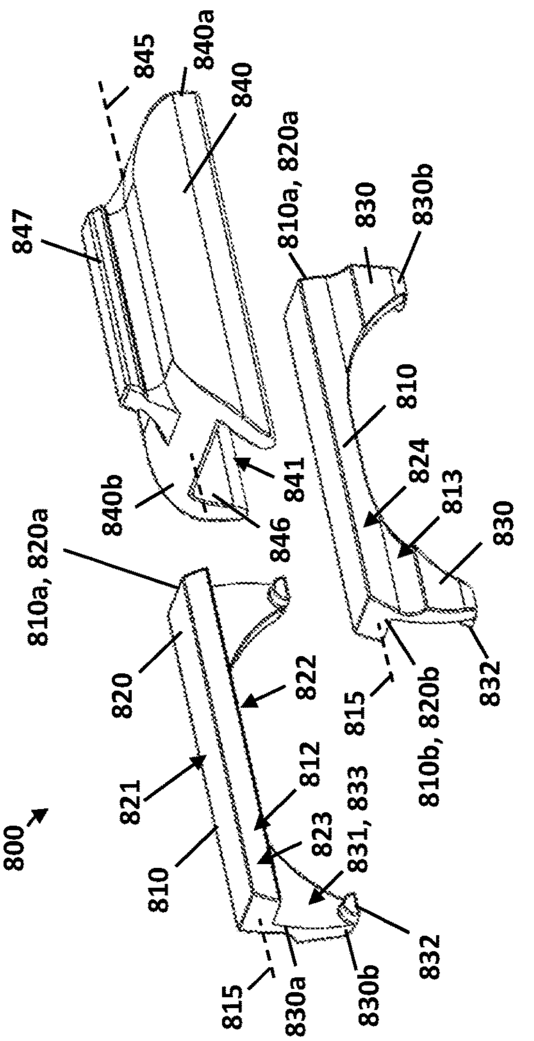
FIG. 26 is an exploded isometric view of the retention device of FIG. 23.
Figure 25:
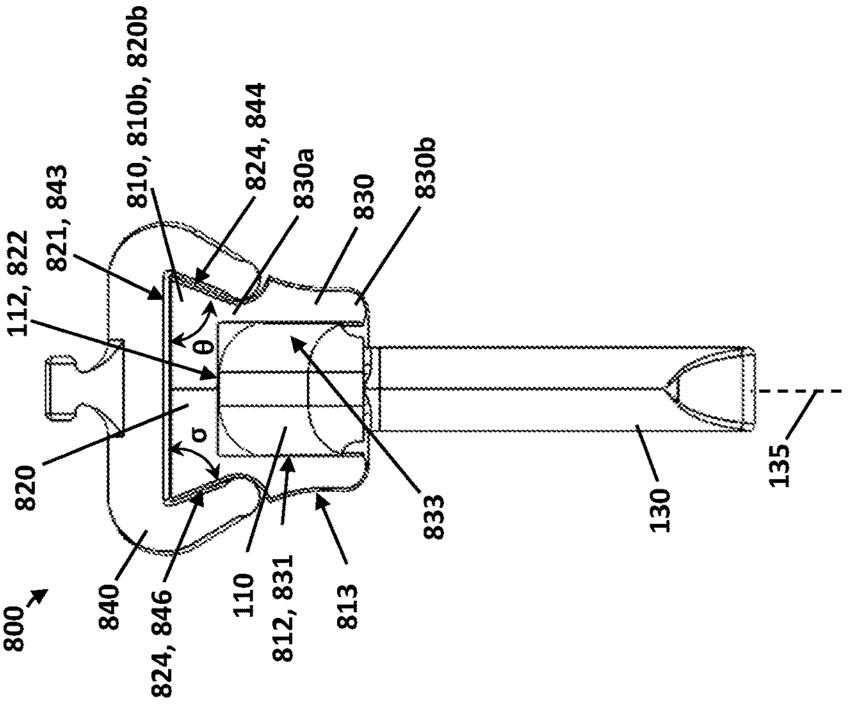
FIG. 25 is a side view of the retention device of FIG. 23.

In this embodiment, retention device 800 has a central or longitudinal axis 805, and includes a pair of implant engagement members 810 and a slide block 840 releasably coupled to engagement members 810 with a dovetail joint 850. Engagement members 810 define a male portion 851 of dovetail joint 850, while slide block 840 defines a female portion 852 of dovetail joint 850 that receives male portion 851. As will be described in more detail below, when slide block 840 is mounted to engagement member 810 as shown in FIGS. 23-25, engagement members 810 are static relative to each other for securing implant 100 therebetween, and when slide block 840 is slidably decoupled (e.g., slid off) engagement members 810 as shown in FIG. 26, engagement members 810 are free to move relative to each other and release implant 100. Thus, retention device 800 and engagement members 810 may be described has having a first or closed configuration for securely gripping and holding implant 100, and a second or open configuration for disengaging and releasing implant 100. In FIGS. 23-25, retention device 800 and engagement members 810 are shown in the first configuration securely holding implant 100; in FIG. 26, retention device 800 and engagement members 810 are shown in the second configuration decoupled from implant 100; and in FIG. 27, retention device 800 and engagement members 810 are shown being transitioned between the first and second configurations by moving slide block 840 axially relative to engagement members 810.

Each engagement member 810 is the same, and thus, only one engagement member 810 will be described it being understood the other engagement member 810 is the same. Engagement member 810 is a rigid single-piece, monolithic, elongate structure having a central or longitudinal axis 815 oriented parallel to axis 805 in the closed configuration, a first end 810*a*, and a second end 810*b* opposite end 810*a*. As shown in FIGS. 23-24, when retention device 800 and engagement members 810 are in the first or closed position, one lateral side of each engagement member 810 faces the other engagement member 810, and the opposite lateral side of each engagement member 810 faces away from the other engagement member 810. Accordingly, engagement member 810 may be described as having an inner side 812 extending between ends 810*a*, 810*b* and an outer side 813 extending between ends 810*a*, 810*b*; with the understanding inner side 812 faces the other engagement member 810 when retention device 800 and engagement members 810 are in the closed position and outer side 813 faces away from the other engagement member 810 when retention device 800 and engagement members 810 are in the closed position.

As best shown in FIG. 26, engagement member 810 includes an elongate body 820 extending axially from end 810*a* to end 810*b* and a pair of arms 830 extending downward from body 820. One arm 830 extends downward from body 820 at each end 810*a*, 810*b*. Body 820 has a first end 820*a* defining end 810*a* of engagement member 810, a second end 820*b* defining end 810*b* of engagement member 810, a planar top surface 821 extending axially from end 820*a* to end 820*b*, a planar lower surface 822 extending axially from end 820*a* to end 820*b*, a planar inner surface 823 extending axially from end 820*a* to end 820*b* along inner side 812, and a planar outer surface 824 extending axially from end 820*a* to end 820*b* along outer side 813. Top surface 821 and lower surface 822 are oriented parallel to each other. Inner surface 823 extends perpendicularly from top surface 821 to lower surface 822, and planar outer surface 824 slopes laterally inward as it extends downward from top surface 821. Thus, in the end view of FIG. 25, planar outer surface 824 is oriented at an acute angle θ relative to top surface 821. As will be described in more detail below, in the closed configuration of retention device 800, planar inner surfaces 823 of engagement members 810 abut and slidingly engage each other, and surfaces 821, 824 of engagement members 810 define the outer profile of male portion 851 of the dovetail joint 850.

As previously described, arms 830 extends downward from body 820 at each end 820*a*, 820*b*. Thus, each arm 830 has a first or fixed end 830*a* fixably secured to and integral with body 820 and a second or free end 830*b* distal body 811. In addition, each arm 830 has a planar surface 831 disposed along inner side 812 and a projection or tip 832 that extends laterally inward from planar surface 831 at free end 830. Planar surface 831 of each arm 830 extends perpendicularly downward from lower surface 822 of body 820. Accordingly, surfaces 822, 831 and tip 832 generally define a C-shaped pocket or recess 833 along inner side 812 at each arm 830.

Similar to tips 541 and pockets 544 of insertion device 500 previously described, each tip 832 is sized and shaped to mate and conform with a corresponding recess 146 of bridge 110 and each pocket 833 is sized to receive a corresponding lateral side of bridge 110 adjacent and above the recess 146.

As previously described, legs 130 of implant 100 are inwardly biased and/or manufactured such that leg angles α increase and ends 130*b* move toward each other upon the application of heat. As best shown in FIG. 25, arms 830 are sized and tips 832 are positioned relative to body 820 such that upper surface 112 of bridge 110 contacts lower surface 822 of body 820 and ends 110*a*, 110*b* of bridge 110 are held in position by tips 832 with central axes 135 of legs 130 oriented parallel to central axes 105 (i.e., leg angles α are 0°) when retention device 800 in the closed configuration and tips 832 are fully seated in mating recesses 146. To provide additional stability, in this embodiment, the lateral sides of bridge 110 contact planar surfaces 831 of arms 830 when retention device 800 in the closed configuration and tips 832 are fully seated in mating recesses 146.

Figure 27:
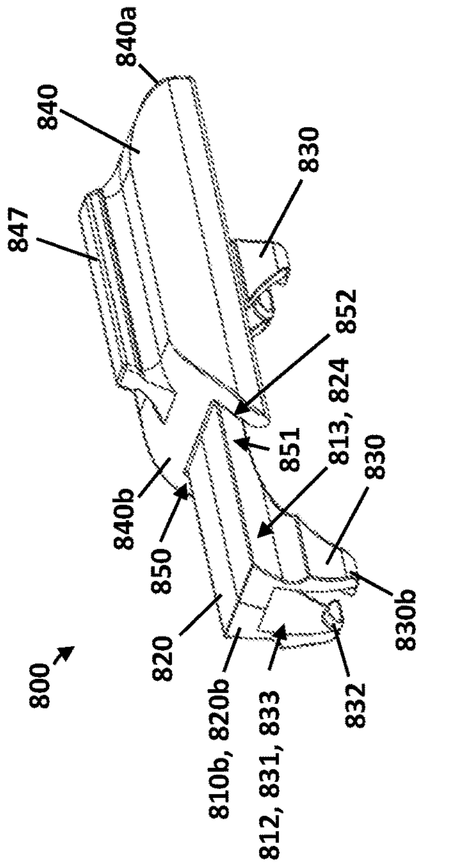
FIG. 27 is an isometric view of the retention device of FIG. 23 illustrating the sliding engagement of the slide block and the implant engagement members.

Referring now to FIGS. 25-27, slide block 840 is a rigid single-piece, monolithic, elongate structure having a central axis 845 oriented parallel to axes 805, 815, a first end 840*a*, and a second end 840*b* opposite end 840*a*. In addition, slide block 840 includes a recess 841 extending axially from first end 840*a* to second end 840*b* along the bottom of slide block 840 and a handle 847 on the top of slide block 840. Recess 841 is defined by a planar top surface 843 and lateral planar surfaces 844, 846 extending downward from top planar surface 843. Recess 841 defines the profile of female portion 852 of dovetail joint 850. In end view of FIG. 25, each lateral planar surface 844, 846 is disposed at an acute angle σ relative to top planar surface 843. To ensure a mating, sliding fit between male portion 851 and female portion 852 of dovetail joint 850, each acute angle θ, σ is the same, thereby allowing planar surface 843 to slidingly engages planar surfaces 821 of both engagement members 820, while each planar surface 844, 846 slidingly engages planar surface 824 of one engagement member 820.

To securely grab and hold implant 100 within retention device 800, axes 135 of legs 130 are held in parallel orientation while each engagement member 810 is disposed along a corresponding lateral side of bridge 110 with inner side 812 facing bridge 110 and tips 832 aligned with recesses 146. Next, while axes 135 of legs 130 are maintained in parallel orientation, engagement members 810 are pushed together to seat tips 832 in recesses 146, bring inner planar surfaces 823 into flush engagement, and bring planar surfaces 831 of arms 830 into engagement with bridge 110. With engagement members 810 held together, recess 841 of slide block 840 is axially aligned with bodies 820 so that female portion 852 defined by recess 841 is positioned to receive male portion 851, and then slide block 840 is moved axially relative to engagement members 810 as shown in FIG. 27 to fully receive male portion 851 into female portion 852 and form dovetail joint 850 and transition retention device 800 to the closed configuration. Once dovetail joint 850 is formed, sliding engagement of planar surfaces 843, 821 and sliding engagement of planar surfaces 844, 846 and planar surfaces 824 prevents engagement members 810 from moving laterally apart and disengaging implant 100. With implant 100 securely held between engagement members 810 with axes 135 of legs 130 oriented parallel to each other and retention device 800 in the closed configuration, a surgeon or user can hold and manipulate handle 847 of retention device 800 to move and position implant 100. In general, the foregoing steps can be performed in reverse to decouple dovetail joint 850 and transition retention device 800 to the open configuration, thereby allowing engagement members 810 to be pulled laterally apart to disengage and release implant 100.

Referring now to FIGS. 28-31, an embodiment of a retention device 900 for holding and positioning staple-style implant 100 is shown. As will be described in more detail below, device 900 can be operated by a surgeon or other user to securely hold implant 100.

Figure 29:
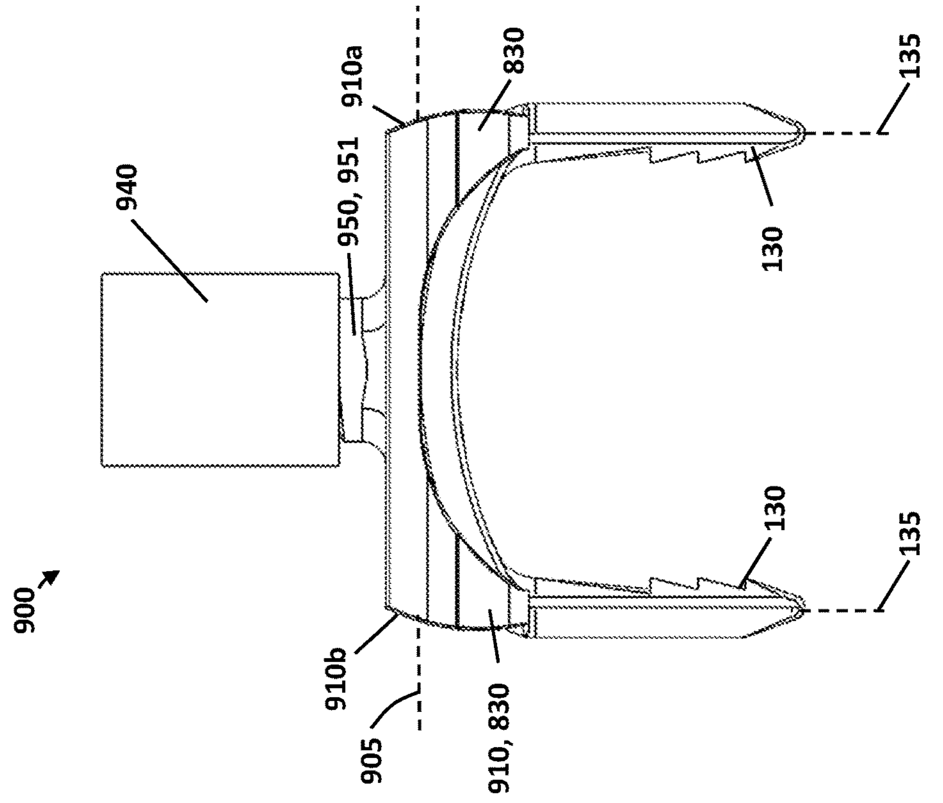
FIG. 29 is a front view of the retention device of FIG. 28.
Figure 28:
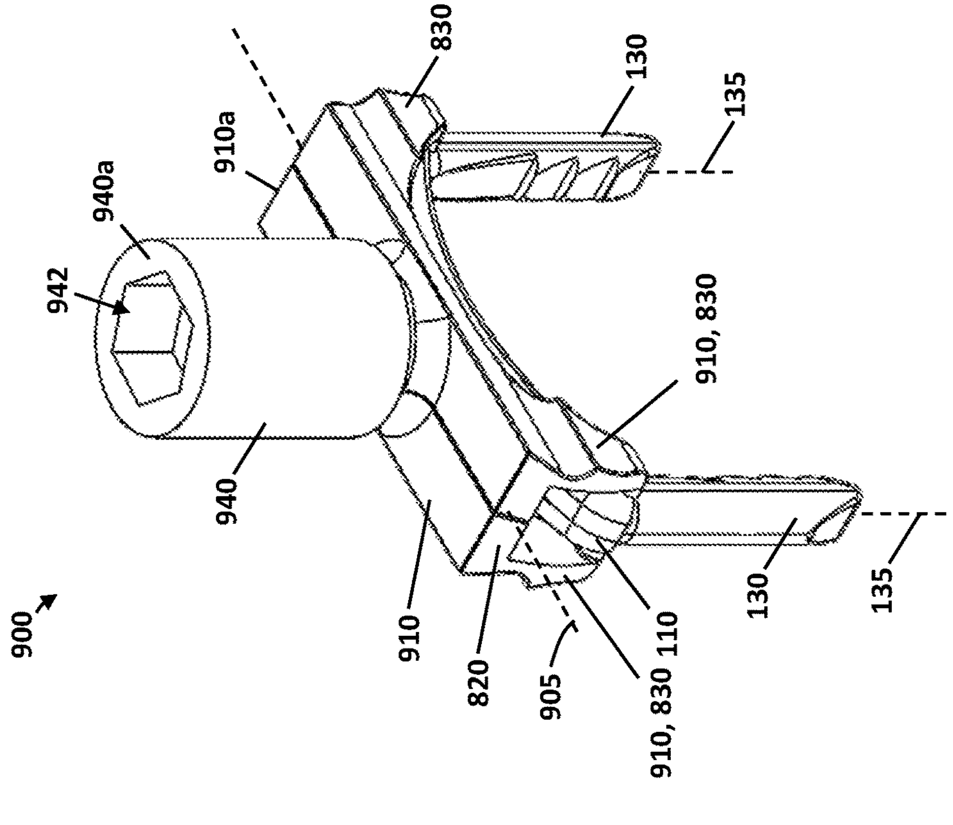
FIG. 28 is an isometric view of an embodiment of a retention device for holding and manipulating embodiments of implants disclosed herein in accordance with the principles described herein.
Figure 31:
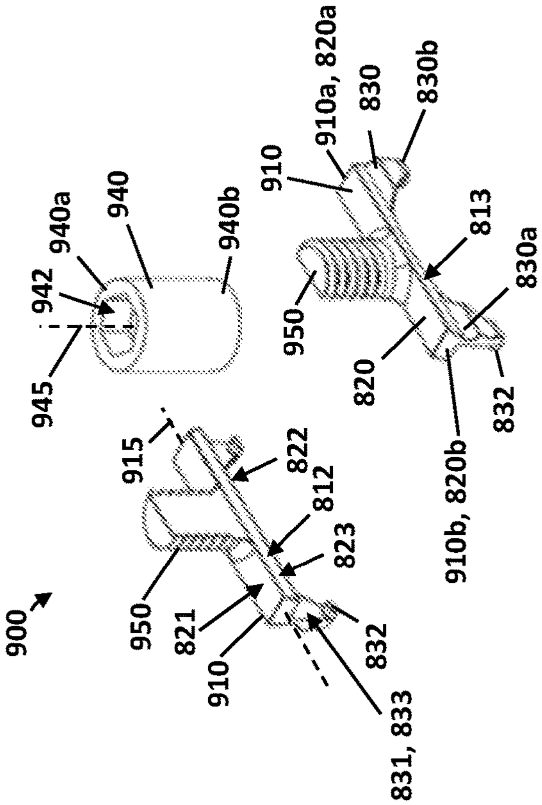
FIG. 31 is an exploded isometric view of the retention device of FIG. 28.
Figure 30:
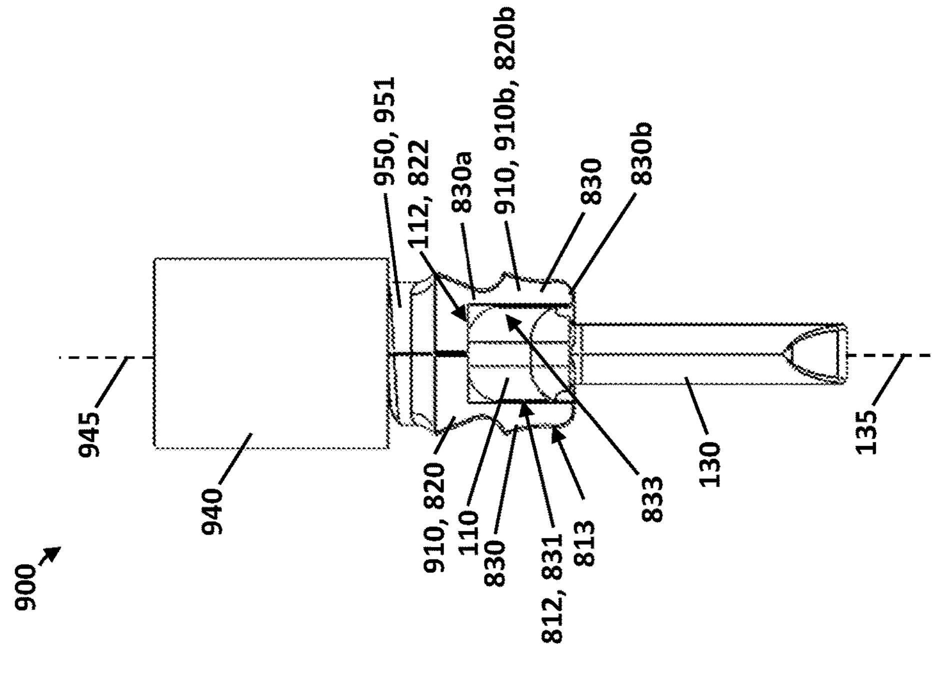
FIG. 30 is a side view of the retention device of FIG. 28.

Retention device 900 is substantially the same as retention device 800 previously described with the exception that slide block 840 is replaced with a locking nut 940. More specifically, in this embodiment, retention device 900 has a central or longitudinal axis 905, and includes a pair of implant engagement members 910 and locking nut 940 releasably coupled to engagement members 910 via mating threads. When locking nut 940 is mounted to engagement member 910 as shown in FIGS. 28-30, engagement members 910 are static relative to each other for securing implant 100 therebetween, and when locking nut 940 is decoupled from engagement members 910 as shown in FIG. 31, engagement members 810 are free to move relative to each other and release implant 100. Thus, retention device 900 and engagement members 910 may be described has having a first or closed configuration for securely gripping and holding implant 100, and a second or open configuration for disengaging and releasing implant 100. In FIGS. 28-30, retention device 900 and engagement members 910 are shown in the first configuration securely holding implant 100; and in FIG. 31, retention device 900 and engagement members 910 are shown in the second configuration decoupled from implant 100.

As best shown in FIG. 31, each engagement member 910 is the same, and thus, only one engagement member 910 will be described it being understood the other engagement member 910 is the same. Engagement member 910 is substantially the same as engagement member 810 previously described. In particular, engagement member 910 is a rigid single-piece, monolithic, elongate structure having a central or longitudinal axis 915 oriented parallel to axis 905, a first end 910*a*, and a second end 910*b* opposite end 910*a*. In addition, engagement member 910 includes an elongate body 820 extending axially from end 910*a* to end 910*b* and a pair of arms 830 extending downward from body 820. Body 820 and arms 830 are as previously described with respect to retention device 800. However, in this embodiment, a semi-cylindrical shaft 950 extends upward from planar top surface 821. Shafts 950 are centered along the length of body 820 such that when engagement members 910 are pushed together as shown in FIGS. 28-30, semi-cylindrical shafts 950 come together to form an externally threaded cylindrical shaft 951.

Figure 32:
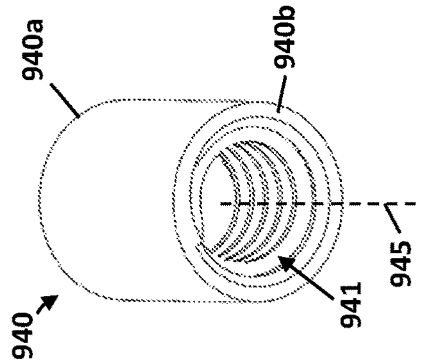
FIG. 32 is an isometric view bottom view of the locking nut of the retention device of FIG. 28.

Referring now to FIGS. 31 and 32, locking nut 940 has a central axis 945, a first or upper end 940*a*, a second or lower end 940*b*, an internally threaded bore 941 extending axially from lower end 940*b*, and a keyed recess 942 extending axially from upper end 940*a*. In this embodiment, keyed recess 942 has a hexagonal cross-sectional geometry in a plane oriented perpendicular to axis 945, and thus, is configured to receive a mating hexagonal shaped key. Internally threaded bore 941 is configured to mate and threadably engage externally threaded shaft 951. It should be appreciated that when locking nut 940 is threaded onto shaft 951, engagement members 910 are fixably coupled such that members 910 cannot move translationally or rotationally relative to each other, whereas when locking nut 940 is unthreaded from shaft 951, engagement members 910 are decoupled and can move relative to each other.

Referring again to FIGS. 28-30, similar to retention device 800 previously described, retention device 900 is configured to receive implant 100 with central axes 135 of legs 130 oriented parallel to each other, and to hold implant 100 with central axes 135 of legs 130 oriented parallel to each other. More specifically, to securely grab and hold implant 100 within retention device 900, axes 135 of legs 130 are held in parallel orientation while each engagement member 910 is disposed along a corresponding lateral side of bridge 110 with inner side 812 facing bridge 110 and tips 832 aligned with recesses 146. Next, while axes 135 of legs 130 are maintained in parallel orientation, engagement members 910 are pushed together to seat tips 832 in recesses 146, bring inner planar surfaces 823 into flush engagement, bring planar surfaces 831 of arms 830 into engagement with bridge 110, and bring semi-cylindrical shafts 950 together to form cylindrical shaft 951. With engagement members 910 held together, retention nut 940 is positioned above and coaxially aligned with shaft 951 with bore 941 positioned to receive shaft 951, and then retention nut 940 is lowered to receive shaft 951 into bore 941 while retention nut 940 is rotated to thread nut 940 onto shaft 951. Nut 940 can be rotated by hand or with a tool having a key that mates with keyed recess 942 such as an Allen wrench.

With implant 100 securely held between engagement members 910 with axes 135 of legs 130 oriented parallel to each other and retention device 900 in the closed configuration, a surgeon or user can hold and manipulate retention nut 940 of retention device 900 to move and position implant 100. The surgeon or user can also employ other tools such as a tamp for use with retention device 900 via mating engagement with keyed recess 942 of retention nut 940. In general, the foregoing steps can be performed in reverse to decouple retention nut 940 and transition retention device 900 to the open configuration, thereby allowing engagement members 910 to be pulled laterally apart to disengage and release implant 100.

As previously described, embodiments of insertion devices 500, 600, 700 and retention devices 800, 900 are configured to receive and securely hold staple-style implants (e.g., implant 100) with the legs of the implant (e.g., legs 130) oriented parallel to each other. In other words, devices 500, 600, 700, 800, 900 may not be configured to transition the legs of the implant from an inwardly biased orientation to a parallel orientation, but rather are configured to maintain and hold the legs of the implant in the parallel orientation. Accordingly, in embodiments where the legs of the implant are inwardly biased, the implant is preferably transferred to the insertion device or the retention device with the legs already oriented parallel to each other. An exemplary embodiment of a device that can hold the legs of a staple-style implant in parallel orientation and transfer the implant to an insertion device or retention device with the legs in parallel orientation will now be described. The exemplary embodiment will be shown and described in connection with implant 100 and insertion device 500 as previously described, however, it should be appreciated that the exemplary embodiments can be used with other embodiments of staple-style implants such as implants 200, 300, 400, 480 and/or other embodiments of insertion or retention devices such as devices 600, 700, 800, 900.

Figure 33:
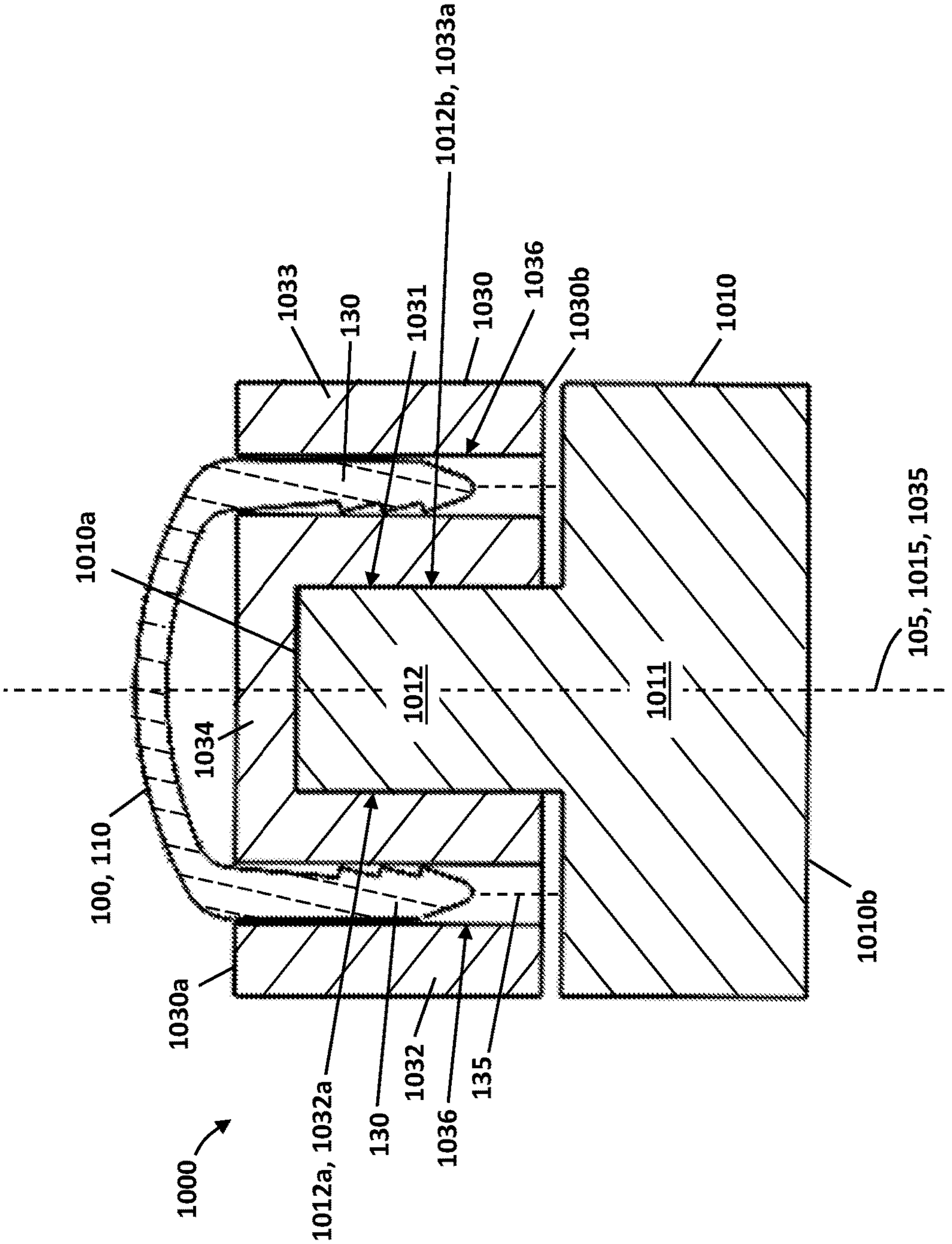
FIG. 33 is a cross-sectional front view of an embodiment of a transfer block in accordance with the principles described herein for holding the legs of a staple-style implant parallel to each other during shipping, handling, storage, and transfer to another device.

Referring now to FIG. 33, an embodiment of a transfer block assembly 1000 for holding the inwardly biased legs 130 of implant 100 in parallel and transferring the implant 100 to insertion device 500 with the legs 130 in parallel is shown. In general, transfer block assembly 1000 can be used to support and maintain legs 130 in parallel during shipping, handling, storage, and transfer to another device such as insertion device 500, which will be described in more detail below. In this embodiment, transfer block assembly 1000 is a two-component structure including a rigid base or key block 1010 and a hinged block 1030 slidably and releasably coupled to base block 1010. Key block 1010 has a central axis 1015, a first or upper end 1010*a*, and a second or lower end 1010*b*. In addition, key block 1010 includes a body 1011 and a projection or key 1012 extending axially from body 1011. Body 1011 defines lower end 1010*b*, and key 1012 extends axially from body 1011 to upper end 1010*a*. In this embodiment, key 1012 is laterally centered on body 1011 (i.e., key 1012 has a central axis coaxially aligned with central axis 1015). Key 1012 is fixably secured and/or integral with body 1011 such that key 1012 and body 1011 cannot move translationally or rotationally relative to each other. In addition, base 1011 is a solid, rigid, rectangular prismatic structure; and key 1012 is a solid, rigid, rectangular prismatic structure.

Referring still to FIG. 33, hinged block 1030 has a central axis 1035, a first or upper end 1030*a*, and a second or lower end 1030*b*. In addition, hinged block 1030 includes a recess 1031 extending axially from lower end 1030*b* toward upper end 1030*a*. In this embodiment, recess 1031 is laterally centered (i.e., recess 1031 has a central axis coaxially aligned with central axis 1035). Recess 1031 generally divides hinged block 1030 into a first leg receiving block 1032 and a second leg receiving block 1033 laterally spaced from block 1032 in front view. Recess 1031 extends axially to a position proximal upper end 1030*a*, thereby defining a relatively thin flexible joint 1034 disposed between leg receiving blocks 1032, 1033 in front view. Joint 1034 extends laterally from first receiving block 1032 to second receiving block 1033 and allows leg receiving blocks 1032, 1033 to pivot relative to each other about an axis the extends through joint 1034, and is oriented orthogonal to axis 1035 and perpendicular to a plane that bisects hinged block 1030 in top view (i.e., the plane in which the cross-section in FIG. 33 is shown). Each leg receiving block 1032, 1033 includes a bore 1036 extending axially from upper end 1030*a* to lower end 1030*b*. Bores 1036 are sized, spaced, and positioned to receive the legs of a staple-style implant (e.g., legs 130 of implant 100). As shown in FIG. 33, in this embodiment, each bore 1036 is cylindrical and has a width or diameter that is slightly greater than the maximum width of the corresponding leg measured perpendicular to the central axis of the leg (e.g., the maximum width of leg 130 measured perpendicular to central axis 135). In embodiments, described herein, the diameter of each bore 1036 is equal to or less than 5% greater than the maximum width of the corresponding leg, alternatively equal to or less than 3% greater than the maximum width of the corresponding leg, and alternatively equal to or less than 1% greater than the maximum width of the corresponding leg 130. As will be described in more detail, by slightly oversizing bores 1036 relative to legs 130, some minor flexing of legs 130 can be accommodated without serrations 138 digging into leg receiving blocks 1032, 1033.

Recess 1031 is sized and shaped to receive and mate with key 1012 of key block 1010. Thus, in this embodiment, recess 1031 has a rectangular prismatic shape with dimensions that are substantially the same as the dimensions of key 1012 to facilitate sliding engagement of key 1012 with leg receiving blocks 1032, 1033. In particular, key 1012 includes planar lateral surfaces 1012*a*, 1012*b* and leg receiving blocks 1032, 1033 include opposed planar lateral surfaces 1032*a*, 1033*a*, respectively, that face each other and slidingly engage planar surfaces 1012*a*, 1012*b*, respectively. As previously described, key 1012 is a solid rigid structure, and thus, when key 1012 is seated in mating recess 1031 with surfaces 1012*a*, 1012*b* slidingly engaging surfaces 1032*a*, 1033*a*, respectively, leg receiving blocks 1032, 1033 are prevented from pivoting laterally inward toward each other. However, when key 1012 is removed from recess 1031, leg receiving blocks 1032, 1033 can pivot laterally inward toward each other as joint 1034 flexes. Accordingly, transfer block assembly 1000, key 1012, and hinged block 1030 may be described as having a first or locked position with key 1012 seated in mating recess 1031 and leg receiving blocks 1032, 1033 prevented from pivoting laterally inward toward each other; and a second or unlocked position with key 1012 removed from recess 1031 and leg receiving blocks 1032, 1033 allowed to pivot laterally inward toward each other. As shown in FIG. 33, when transfer block assembly 1000, key 1012, and hinged block 1030 are in the locked position(s), bores 1036 are oriented parallel to each other and axes 1015, 1035, and thus, are positioned and oriented to receive and maintain legs 130 of implant 100 oriented parallel to each other.

As previously described, transfer block assembly 1000 can be used to support and maintain legs 130 in parallel during shipping, handling, storage, and transfer to another device. More specifically, transfer block assembly 1000 is arranged in the locked position with legs 130 of implant 100 seated in recesses 1036. As long as transfer block assembly 1000 remains in the locked position, the otherwise inwardly biased legs 130 of implant 100 remain oriented parallel to each other.

Figure 35:
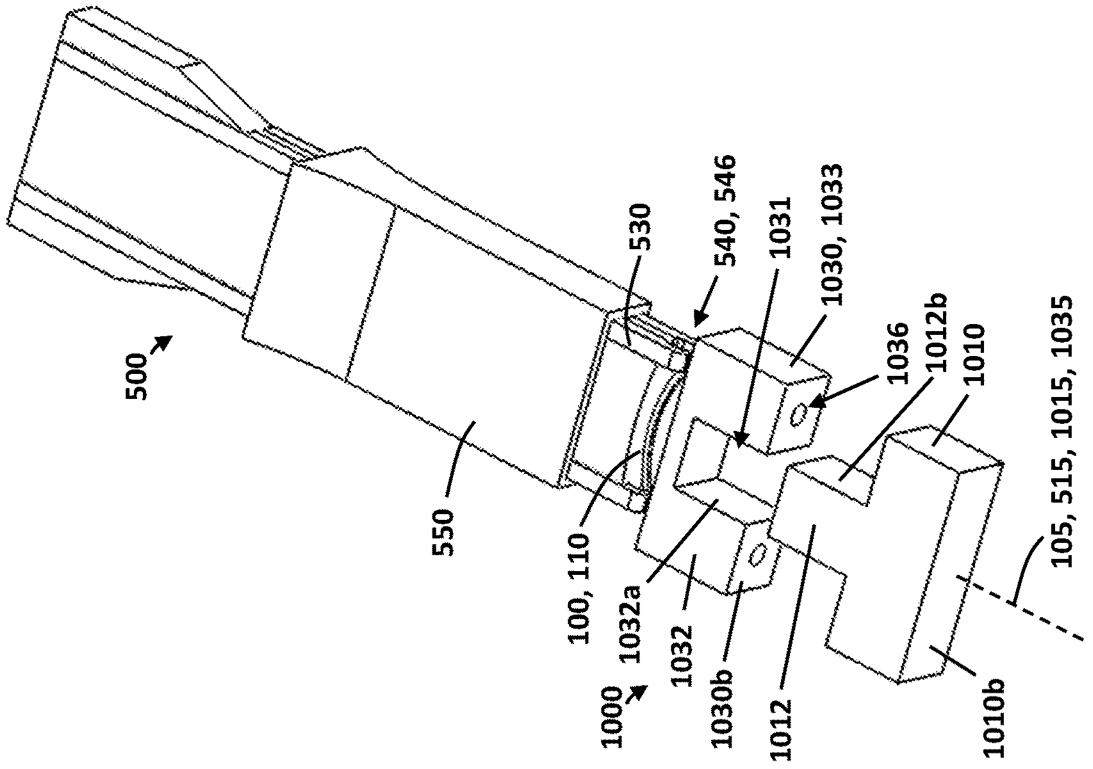
FIGS. 34 and 35 are perspective views illustrating the transfer of the implant of FIG. 2 from the transfer block of FIG. 33 to the insertion device of FIG. 11.
Figure 34:
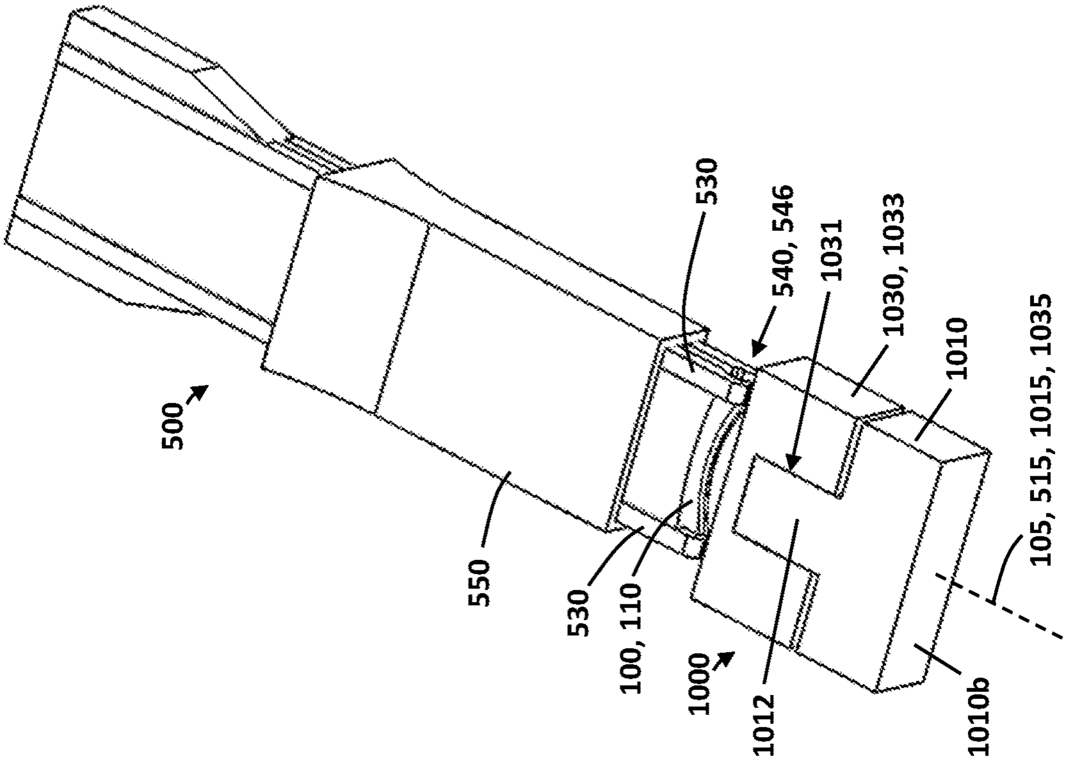

Referring now to FIGS. 34 and 35, transfer block assembly 1000 is shown transferring implant 100 to insertion device 500 with legs 130 oriented parallel to each other. Starting at FIG. 34, implant 100 is mounted to transfer block assembly 1000 with legs 130 seated in bores 1036 and transfer block assembly 1000 in the locked position as shown in FIG. 33. Thus, bores 1036 and legs 130 are oriented parallel to each other. Next, insertion device 500 securely engages bridge 110 of implant 100 by transitioning jaws 546 to the open positions (sliding sleeve 550 axially upward away from end 510*b*), receiving ends 110*a*, 110*b* in jaws 546, and then transitioning jaws 546 to the closed positions (sliding sleeve 550 axially downward toward end 510*b*) with tips 541 seated in mating recesses 146 and engaging shoulders 142. Transfer block assembly 1000 is in the locked position, and thus, insertion device 500 securely engages bridge 110 of implant 100 with legs 130 oriented parallel to each other.

Moving now to FIG. 35, after insertion device 500 securely engages bridge 110 of implant 100 with legs 130 oriented parallel to each other, transfer block assembly 1000 is transitioned to the unlocked position by moving key block 1010 and hinged block 1030 axially apart to remove key 1012 from recess 1031. When transfer block assembly 1000 is in the locked position, key 1012 bears the compressive forces exerted by inwardly biased legs 130 and prevents leg receiving blocks 1032, 1033, and hence prevents legs 130, from pivoting laterally inward toward each other about joint 1034. Thus, when transfer block assembly 1000 is transitioned to the unlocked position by removal of key 1012 from recess 1031, key 1012 not longer bears the compressive forces exerted by inwardly biased legs 130. However, as previously described, with jaws 546 of insertion device 500 securing engaging ends 110*a*, 110*b* of bridge 110 in the closed positions, insertion device 500 can effectively bear the compressive forces exerted by inwardly biased legs 130 by applying loads to ends 110*a*, 110*b* of bridge 110 to maintain legs 130 in parallel orientation relative to each other. It should be appreciated that hinged block 1030 alone (without the aid of insertion device 500) cannot bear the compressive forces exerted by inwardly biased legs 130 as once key 1012 is removed from recess 1031, flexion at joint 1034 allows leg receiving blocks 1032, 1033 to pivot inwardly toward each other. Therefore, as transfer block assembly 1000 is transitioned from the locked position to the unlocked position as shown in FIGS. 34 and 35, the compressive loads exerted by inwardly biased legs 130 are transferred from transfer block assembly 1000 to insertion device 500.

With key 1012 withdrawn from recess 1031 and transfer block assembly 1000 in the unlocked position, implant 100 can be withdrawn from hinged block 1030 with insertion device 500 while insertion device 500 maintains legs 130 in the parallel orientation. In particular, with jaws 546 securely engaging bridge 110 of implant, insertion device 500 and hinged block 1030 are moved axially apart to pull legs 130 from bores 1036.

It should be appreciated that there may be some relatively minor flexing of legs 130 as key 1012 is withdrawn from recess 1031 and/or as legs 130 are pulled from bores 1036. For example, if compressive loads are applied to the outside of leg receiving blocks 1032, 1033 to grasp and hold hinged block 1030 as key 1012 withdrawn from recess 1031 or as legs 130 are pulled from bores 1036 after withdrawal of key 1012, legs 130 may flex radially inward. Serrations 138 may undesirably cut or tear small pieces of hinged block 1030 if permitted to slidingly engagement hinged block 1030 within bores 1036 in response to such flexing of legs 130. Any such small cuttings of hinged block 1030 should preferably be avoided so as not to inadvertently be transferred to the patient. Accordingly, small clearances are provided between hinged block 130 and legs 130 disposed in bores 1036 as previously described (i.e., bores 1036 may have diameters that are slightly larger than the maximum widths of legs 130), and further, hinged block 1030 is permitted to flex at joint 1034 in response to any flexing of legs 130. Such features reduce and/or avoid compressive loads at the interfaces between legs 130 and hinged block 1030, thereby offering the potential to reduce and/or eliminate cutting of hinged block 1030 with serrations 138 of legs 130, as well as reduce the axial forces that must be applied to pull implant 100 from hinged block 1030 with insertion device 500.

In the manner described, embodiments disclosed herein include staple-style implants that may include rounded or partially rounded legs that maximize strength within a given drilled hole. In addition, some embodiments disclosed herein include implant bridges which have a different cross-sectional shape than the corresponding legs. In particular, the cross-section of the bridge may include a partially rounded profile that provides a low implant profile and establishes a more anatomically conforming fit. Embodiments of devices for holding, positioning, and/or installing staple-style implants are also disclosed herein.

While exemplary embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. An orthopedic compression implant for applying compression between a first bone segment and a second bone segment, the orthopedic compression implant comprising:

a bridge having a longitudinal axis, a first end, and a second end opposite the first end, wherein the bridge has a radially outer surface extending axially relative to the longitudinal axis from the first end to the second end;

a first leg extending from the first end of the bridge, wherein the first leg has a central axis, a fixed end fixably attached to the bridge, a free end distal the bridge, and a radially outer surface extending axially relative to the central axis of the first leg from the fixed end of the first leg to the free end of the first leg; and a second leg extending from the second end of the bridge, wherein the second leg has a central axis, a fixed end fixably attached to the bridge, a free end distal the bridge, and a radially outer surface extending axially relative to the central axis of the second leg from the fixed end of the second leg to the free end of the second leg;

wherein the longitudinal axis of the bridge, the central axis of the first leg, and the central axis of the second leg are disposed in a common reference plane;

wherein the radially outer surface of the bridge includes a lower surface that extends axially relative to the longitudinal axis from the first end of the bridge to the second end of the bridge, intersects the fixed ends of the first leg and the second leg, and has a width measured perpendicular to the common reference plane that is greater than a width of each leg measured perpendicular to the common reference plane such that the lower surface extends laterally beyond the first leg and the second leg;

wherein the radially outer surface of the bridge defines a first outer profile in a cross-section of the bridge taken in a plane oriented perpendicular to the longitudinal axis of the bridge, wherein the radially outer surface of the first leg defines a second outer profile in a cross-section of the first leg taken in a plane oriented perpendicular to the central axis of the first leg, wherein the second outer profile is non-rectangular, and wherein the first outer profile has a different geometry than the second outer profile;

wherein the orthopedic compression implant has a central axis disposed in the common reference plane, positioned between the central axes of the first leg and the second leg, and intersecting the longitudinal axis of the bridge;

wherein the first leg is oriented at a first leg angle $\alpha$ measured in the common reference plane between the central axis of the first leg and the central axis of the orthopedic compression implant, wherein the second leg is oriented at a second leg angle $\alpha$ measured in the common reference plane between the central axis of the second leg and the central axis of the orthopedic compression implant;

wherein the legs have;

(i) a first position with the central axis of the first leg oriented substantially parallel to the central axis of the second leg and each leg angle $\alpha$ equal to approximately 0°; and (ii) a second position with each leg angle $\alpha$ greater than 0° and the legs sloping towards each other and the central axis of the orthopedic compression implant moving axially relative to the central axis of the corresponding leg from the fixed end of the corresponding leg to the free end of the corresponding leg, wherein the legs are biased to the second position;

wherein the first leg is configured to be inserted in a first hole in the first bone segment and the second leg is configured to be inserted in a second hole in the second bone segment with the legs in the first position;

wherein the longitudinal axis of the bridge is continuously curved in the common reference plane moving axially along the bridge relative to the longitudinal axis of the bridge from the first end of the bridge to the second end of the bridge with the legs in the first position and with the legs in the second position:

wherein the bridge is elastically flexed with the legs in the first position to bias the legs from the first position to the second position.

2. The orthopedic compression implant of claim 1, wherein the first outer profile is non-rectangular.

3. The orthopedic compression implant of claim 2, wherein the first outer profile is D-shaped.

4. The orthopedic compression implant of claim 2, wherein the lower surface of the radially outer surface of the bridge includes a plurality of tool engagement shoulders at the first end of the bridge and a plurality of tool engagement shoulders at the second end of the bridge, wherein the plurality of tool engagement shoulders at the first end of the bridge and the plurality of tool engagement shoulders at the second end of the bridge are configured to be engaged by an external tool to elastically flex the bridge.

5. The orthopedic compression implant of claim 4, wherein each tool engagement shoulder is defined by a planar surface oriented perpendicular to the common reference plane, and wherein the plurality of tool engagement shoulders at the first end of the bridge are positioned laterally adjacent the fixed end of the first leg and the plurality of tool engagement shoulders at the second end of the bridge are positioned laterally adjacent the fixed end of the second leg.

6. The orthopedic compression implant of claim 2, wherein the lower surface of the radially outer surface of the bridge includes a plurality of tool engagement recesses at the first end of the bridge and a plurality of tool engagement recesses at the second end of the bridge.

7. The orthopedic compression implant of claim 6, wherein each tool engagement recess of the bridge is at least partially cylindrical.

8. The orthopedic compression implant of claim 1, wherein the radially outer surface of the first leg comprises a plurality of axially spaced serrations.

9. The orthopedic compression implant of claim 8, wherein the radially outer surface of the second leg comprises a plurality of axially spaced serrations that face the plurality of axially-spaced serrations of the first leg.

10. The orthopedic compression implant of claim 1, wherein the central axis of the first leg is not parallel to the central axis of the second leg.

11. The orthopedic compression implant of claim 1, wherein each leg angle $\alpha$ is between approximately 0° and approximately 20° with the legs in the second position.

12. The orthopedic compression implant of claim 1, wherein the lower surface of the radially outer surface of the bridge includes a first plurality of tool engagement recesses and a second plurality tool engagement recesses that are axially spaced relative to the longitudinal axis of the bridge from the first plurality of tool engagement recesses.

13. The orthopedic compression implant of claim 12, wherein the first plurality of tool engagement recesses are positioned proximal the fixed end of the first leg and the second plurality tool engagement recesses are positioned proximal the fixed end of the second leg.

14. The orthopedic compression implant of claim 12, wherein each tool engagement recess of the bridge is at least partially cylindrical.

15. The orthopedic compression implant of claim 1, wherein the longitudinal axis of the bridge has a radius of curvature that varies moving axially along the central axis of the bridge from the first end of the bridge to the second end of the bridge with the legs in the second position.

16. The orthopedic compression implant of claim 1, wherein a cross-sectional area of the bridge in any plane oriented perpendicular to the longitudinal axis of the bridge is equal to or greater than a cross-sectional area of each leg in any plane oriented perpendicular to the central axis of the corresponding leg.

17. The orthopedic compression implant of claim 16, wherein a ratio of the cross-sectional area of the bridge in any plane oriented perpendicular to the longitudinal axis of the bridge to the cross-sectional area of each leg in any plane oriented perpendicular to the central axis of the corresponding leg ranges from 1.5 to 3.0.

18. The orthopedic compression implant of claim 1, wherein the radially outer surface of the bridge includes an upper surface that extends axially relative to the longitudinal axis from the first end of the bridge to the second end of the bridge, wherein the upper surface of the radially outer surface of the bridge is convex in side view perpendicular to the common reference plane with the legs in the first position and with the legs in the second position.

19. An orthopedic compression implant for applying compression between a first bone segment and a second bone segment, the orthopedic compression implant comprising:

a bridge having a longitudinal axis, a first end, a second end opposite the first end, and a radially outer surface extending axially relative to the longitudinal axis from the first end to the second end;

wherein the radially outer surface of the bridge defines a first outer profile in a cross-section of the bridge taken in a plane oriented perpendicular to the longitudinal axis of the bridge, wherein the first outer profile is non-rectangular;

a plurality of legs extending from the bridge, wherein each leg has a central axis disposed in a common reference plane as the longitudinal axis of the bridge, a fixed end fixably attached to the bridge, a free end distal the bridge, and a radially outer surface extending axially from the fixed end of the leg to the free end of the leg;

wherein the radially outer surface of the bridge comprises an upper surface and a lower surface, wherein the lower surface of the radially outer surface of the bridge is concave between the first end of the bridge and the second end of the bridge in the common reference plane in front view;

wherein the lower surface of the radially outer surface of the bridge extends axially from the first end of the bridge to the second end of the bridge, intersects the fixed end of each of the plurality of legs, and has a width measured perpendicular to the common reference plane that is greater than a width of each leg measured perpendicular to the common reference plane such that the lower surface extends laterally beyond each of the plurality of legs; and wherein the upper surface of the radially outer surface of the bridge is convex in the cross-section of the bridge taken in a plane oriented perpendicular to the longitudinal axis of the bridge;

wherein the orthopedic compression implant has a central axis disposed in the common reference plane, positioned between the first end of the bridge and the second end of the bridge, and intersecting the longitudinal axis of the bridge;

wherein the orthopedic compression implant has (i) an elastically flexed position with the central axes of the legs oriented substantially parallel to each other, and (ii) a relaxed position with each leg sloping towards the central axis of the orthopedic compression implant moving axially relative to the central axis of the leg from the fixed end of the leg to the free end of the leg, wherein the orthopedic compression implant is elastically biased to the relaxed position;

wherein the plurality of legs are configured to be inserted in into corresponding holes in the first bone segment and the second bone segment with the orthopedic compression implant in the elastically flexed position;

wherein the longitudinal axis of the bridge is continuously curved in the common reference plane moving axially along the bridge relative to the longitudinal axis of the bridge from the first end of the bridge to the second end of the bridge with the orthopedic compression implant in the elastically flexed position and in the relaxed position.

20. The orthopedic compression implant of claim 19, wherein the radially outer surface of each leg defines a second outer profile in a cross-section of the leg taken in a plane oriented perpendicular to the central axis of the leg, and wherein the second outer profile of each leg is non-rectangular.

21. The orthopedic compression implant of claim 20, the second outer profile of each leg is circular.

22. The orthopedic compression implant of claim 19, wherein each of the plurality of legs includes a cylindrical surface proximate the fixed end, wherein and the lower surface of the radially outer surface of the bridge comprises a plurality of downward facing shoulders positioned between the cylindrical surface of each leg and the upper surface.

23. The orthopedic compression implant of claim 22, wherein the lower surface of the radially outer surface of the bridge includes a plurality of tool engagement recesses at the first end of the bridge and the second end of the bridge.

24. The orthopedic compression implant of claim 22, wherein the plurality of shoulders are configured to receive loads that apply a bending moment to the bridge that increases a radius of curvature of the curved central axis in front view and transition the orthopedic compression implant from the relaxed position to the elastically flexed position.

25. The orthopedic compression implant of claim 19, wherein the lower surface of the radially outer surface of the bridge includes a first plurality of tool engagement recesses and a second plurality tool engagement recesses that are axially spaced relative to the longitudinal axis of the bridge from the first plurality of tool engagement recesses.

26. The orthopedic compression implant of claim 25, wherein the first plurality of tool engagement recesses are positioned proximal the fixed end of one of the plurality of legs and the second plurality tool engagement recesses are positioned proximal the fixed end of another one of the plurality of legs.

27. The orthopedic compression implant of claim 25, wherein each tool engagement recess of the bridge is at least partially cylindrical.

28. The orthopedic compression implant of claim 19, wherein a cross-sectional area of the bridge in any plane oriented perpendicular to the longitudinal axis of the bridge is equal to or greater than a cross-sectional area of each leg in any plane oriented perpendicular to the central axis of the corresponding leg.

29. The orthopedic compression implant of claim 19, wherein the upper surface of the radially outer surface of the bridge is convex in side view perpendicular to the common reference plane with the orthopedic compression implant in the elastically flexed position and in the relaxed position.

30. The orthopedic compression implant of claim 19, wherein the bridge is elastically flexed to bias the orthopaedic compression implant to the relaxed position.

* * * * *